United States Patent
Leichter et al.

(10) Patent No.: US 7,418,119 B2
(45) Date of Patent: *Aug. 26, 2008

(54) DISPLAY FOR COMPUTER-AIDED EVALUATION OF MEDICAL IMAGES AND FOR ESTABLISHING CLINICAL RECOMMENDATION THEREFROM

(75) Inventors: Isaac Leichter, Jerusalem (IL); Philippe Bamberger, Jerusalem (IL); Richard Lederman, Jerusalem (IL)

(73) Assignee: Siemens Computer Aided Diagnosis Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/754,622

(22) Filed: Jan. 12, 2004

(65) Prior Publication Data

US 2004/0184644 A1 Sep. 23, 2004

Related U.S. Application Data

(63) Continuation-in-part of application No. 10/284,213, filed on Oct. 31, 2002, now Pat. No. 7,203,350.

(51) Int. Cl.
G06K 9/00 (2006.01)
(52) U.S. Cl. .................. 382/128; 382/131; 382/132
(58) Field of Classification Search ............ 382/131, 382/128, 132, 133; 424/9.3, 9.4; 378/4, 378/21–33, 901; 128/922
See application file for complete search history.

(56) References Cited

U.S. PATENT DOCUMENTS

| 5,627,907 | A | 5/1997 | Gur et al. |
|---|---|---|---|
| 5,729,620 | A | 3/1998 | Wang |
| 5,815,591 | A | 9/1998 | Roehrig et al. |
| 5,828,774 | A | 10/1998 | Wang |
| 5,832,103 | A | 11/1998 | Giger et al. |
| 5,854,851 | A | 12/1998 | Bamberger et al. |
| 5,970,164 | A | 10/1999 | Bamberger et al. |
| 6,058,322 | A * | 5/2000 | Nishikawa et al. .......... 600/408 |
| 6,075,878 | A | 6/2000 | Yoshida et al. |
| 6,075,879 | A | 6/2000 | Roehrig et al. |
| 6,198,838 | B1 | 3/2001 | Roehrig et al. |
| 6,266,435 | B1 | 7/2001 | Wang |

(Continued)

OTHER PUBLICATIONS

Isaac Leicheter et al. "Computerized diagnostics in digital mammography", I.E.E.E. 1996, pp. 406-408.*

(Continued)

Primary Examiner—Brian Q Le

(57) ABSTRACT

A method for displaying a computer-generated determination of the overall likelihood of malignancy in a mammogram lesion. The method requires providing a digitized image of a mammogram, displaying the digitized image, and selecting a region of interest directly on the displayed digitized image. The digitized image is then processed so that classifier data of the lesion in the user-selected region of interest are generated and displayed. The overall likelihood of malignancy is generated from the classifier data and also displayed. A clinical recommendation for further assessing the lesion is derived from the overall evaluation of malignancy and presented to the user. A system for displaying a determination of the overall likelihood of malignancy in a mammogram lesion and for presenting a clinical recommendation to the user is also provided. A method for integrating the overall likelihood of malignancy with a physician's independent score for the lesion is discussed.

8 Claims, 13 Drawing Sheets

U.S. PATENT DOCUMENTS

| | | | |
|---|---|---|---|
| 6,282,305 B1 * | 8/2001 | Huo et al. ................... | 382/128 |
| 6,285,992 B1 | 9/2001 | Kwasny et al. | |
| 6,434,262 B2 | 8/2002 | Wang | |
| 6,470,092 B1 | 10/2002 | Li et al. | |
| 6,650,766 B1 * | 11/2003 | Rogers et al. ............... | 382/132 |
| 6,999,625 B1 * | 2/2006 | Nelson ....................... | 382/224 |

OTHER PUBLICATIONS

Baoyu Zheng et al., Digital Mammography: Mixed Feature Neural Network with Spectral Entropy Decision for Detection of Microcalcifications, I.E.E.E. Transactions on Medical Imaging, vol. 15, pp. 589-597, Oct. 1996.

M. Naf Gurcan et al., Automated Detection and Enhancement of Microcalcification in Mammograms using Nonlinear Subband Decomposition, I.E.E.E. Acoustics, Speech and Signal Processing, vol. 4, pp. 3069-3072, Apr. 1997.

Jong Kook Kim et al., Statistical Textural Features for Detection of Microcalcifications in Digitized Mammograms, I.E.E.E. Transactions on Medical Imaging, vol. 18, pp. 231-238, Mar. 1999.

A.S. Constantinidis et al., Evaluating classification strategies for detection of circumscribed masses in digital mammograms, I.E.E.E. Imaging Processing and its Applications, vol. 1, pp. 435-439, Jul. 1999.

Songyang Yu et al., A CAD System for the Automatic Detection of Clustered Microcalcifications in Digitized Mammogram Films, I.E.E.E. Imaging, vol. 19, pp. 115-126, Feb. 2000.

Walker H. Land et al., New Results in Breast Cancer Classification Obtained from an Evolutionary Computation/Adaptive Boosting Hybrid Using Mammogram and History Data, I.E.E.E. Soft computing in Industrial Applications, pp. 47-52, Jun. 2001.

Estevez L. W. et al, Computer Assisted Enhancement of mammograms for Detection of microcalcifications, I.E.E.E. Computer-Based Medical Systems, pp. 16-23, Jun. 1995.

* cited by examiner

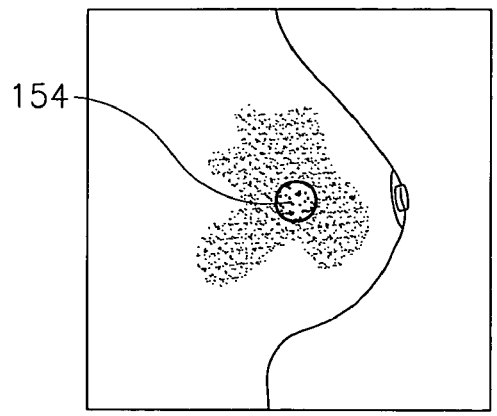
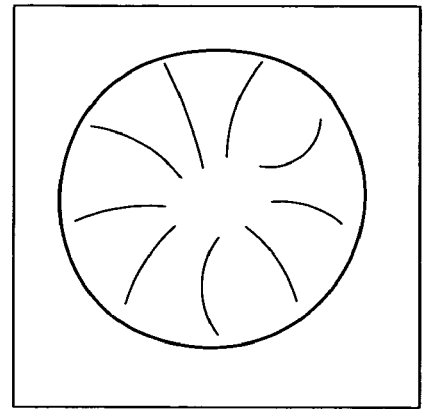
FIG.2A  FIG.2B
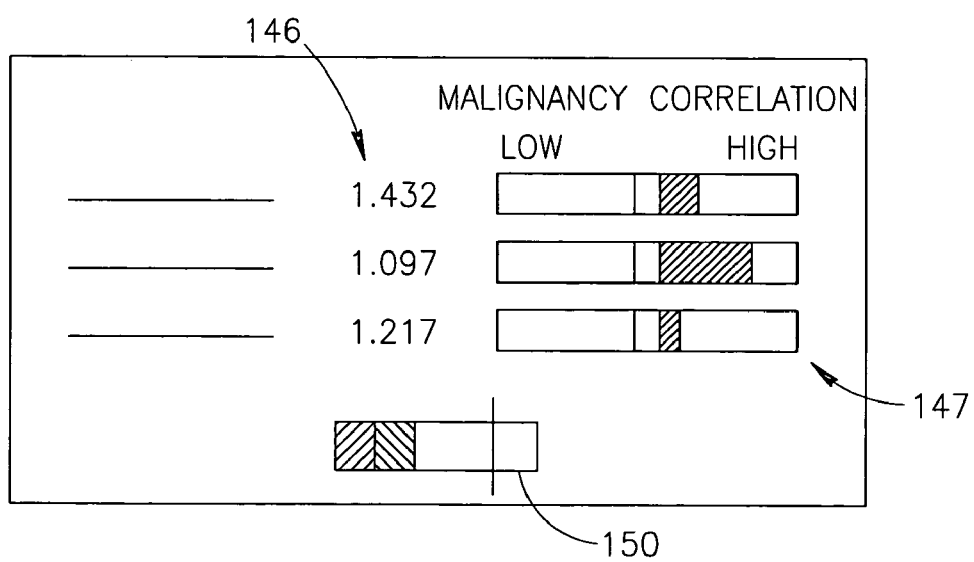
FIG.2C

DISPLAY FOR COMPUTER-AIDED EVALUATION OF MEDICAL IMAGES AND FOR ESTABLISHING CLINICAL RECOMMENDATION THEREFROM

CROSS REFERENCE TO RELATED APPLICATION

This application is a continuation-in-part of U.S. patent application Ser. No. 10/284,213 filed Oct. 31, 2002 entitled "Display for Computer-Aided Diagnosis of Mammograms".

FIELD OF THE INVENTION

The present invention relates to a method and system for displaying evaluation/classification information that assists in determining the malignancy or non-malignancy of abnormalities appearing on radiological mammogram images.

BACKGROUND OF THE INVENTION

Breast cancer is one of the most common types of cancer afflicting Western society. It is estimated that the spread of the disease has risen in the United States, from one in twenty women being afflicted in 1940, to one in eight in 1995. The American Cancer Society estimated that 183,000 new cases of breast cancer were reported during 1995. In the United States, some 46,000 women die from the disease per year. Today, it is accepted that the best way to detect breast cancer in its early stages is by annual mammography screening of women aged 40 and up.

The five-year survival rate for localized breast cancer is 93%. That rate drops to 72% if the cancer has spread regionally by the time of diagnosis. For patients with distant metastases at the time of diagnosis, the five-year survival rate is only 18%. Early diagnosis is thus of great importance to the cure. Since the interpretation of mammographic lesions is problematic, a need for advanced diagnostic tools is required.

The main mammographic findings that may indicate breast cancer are:
1. masses and densities
2. micro-calcifications The characteristics used to determine whether or not masses are malignant are: a) shape (regularity versus irregularity), b) margins (distinct or non-distinct), c) spiculation (thin lines extending from the mass).

The characteristics distinguishing between malignant or benign micro-calcifications are: size, form, pleomorphism within the cluster, cluster shape (if linear or branch-like), spatial density (if crowded or spread out) and relationship to masses.

Today, radiologists generally interpret the mammogram visually, using a light box, and their analysis is largely subjective. Film masking is used to highlight additional detail. In many cases, the radiologist employs supplementary tools such as a magnifying glass and bright light sources to evaluate very dark regions. If the mammogram is not conclusive the radiologist must recall the patient for an additional mammogram using one or more of the following techniques:
1. adding a view with a different projection.
2. performing a magnification mammogram by changing the distance between the breast and the film.
3. locally compressing the breast in the area of suspected abnormality.

The analysis, even after using the above techniques, still remains mainly subjective.

All the statistical data related to the conventional mammogram process were published in scientific literature and concern the U.S. population only. It is assumed that these data are also relevant outside the U.S.

1. Most professional organizations recommend that women over age 40 have a mammography examination once a year.
2. There is a recall rate of about 20%. This is the percentage of patients recalled to perform further examinations, essentially another mammogram.
3. About 3% of women who are evaluated by screening mammography are referred for a biopsy.
4. In screening mammography, about 60 malignancies are found in a sample of 10,000 cases.
5. The false negative rate of the mammographic screening process is difficult to estimate. It is generally accepted that 15% of the women who have ultimately been diagnosed with breast cancer and who had a mammogram performed during the previous 12 months were not originally diagnosed with cancer.
6. The false positive rate of the screening mammography process, i.e. the rate of negative results of biopsies performed due to the screening process, is about 80%.

In order to aid radiologists in reducing the false negative rate in mammographic screening, computer systems using specialized software and/or specialized hardware have been developed. These systems, often called computer-aided detection systems, have been known for many years and have been reported extensively. As noted below, their use in evaluating mammograms has been discussed at length in both the patent and professional literature.

Reading large numbers of mammograms is a difficult and tiring task. According to some literature reports as noted above, unacceptably high rates of false negative results occur. Using computer-aided detection systems provides an independent detection mechanism assisting radiologists in attaining higher malignancy detection rates, i.e. reducing false negative rates.

However, it is well known that computer-aided detection systems almost invariably indicate more suspected abnormalities than are detected by a trained radiologist. The number indicated is often significantly greater than can easily be reviewed. Therefore, a radiologist may have to examine, and must often dismiss, not only the suspected abnormalities that he detects from the radiological mammogram films but also the additional, typically greater number of, suspected abnormalities detected by the computer-aided detection system. Depending on how many more additional suspected abnormalities the computer-aided detection system detects and identifies on the display, the extra work in examining and dismissing these additional abnormalities can slow down the diagnostic process. Even with the use of confidence levels, which usually are insufficiently detailed and nuanced, the task of reviewing the many false locator markers displayed by the system may be more tiresome and troublesome than the benefits that accrue from looking more carefully into the individual suspected lesions.

Computer-aided detection and computer-aided diagnosis (CAD) mammography systems have been discussed extensively in many issued patents. An overview of the field can be obtained by reviewing U.S. Pat. No. 5,729,620 (Wang); U.S. Pat. No. 5,815,591 (Roehrig, et al); U.S. Pat. No. 5,828,774 (Wang); U.S. Pat. No. 5,854,851 (Bamberger, et al); U.S. Pat. No. 5,970,164 (Bamberger, et al); U.S. Pat. No. 6,075,879 (Roehrig, et al); U.S. Pat. No. 6,198,838 (Roehrig, et al); U.S. Pat. No. 6,266,435 (Wang); and U.S. Pat. No. 6,434,262

(Wang). These patents, including references cited therein, are hereby incorporated by reference in this specification as though fully set forth herein.

DEFINITIONS

In what is discussed herein, including the claims, the following terms will be used generally with the following meanings:

Lesion—used interchangeably with suspected or suspicious abnormality without any attempt at distinguishing between them. A lesion or abnormality in a mammogram is generally characterized by a characterization feature as defined below.

Characterization features—anatomical features that typically accompany malignancies and are normally used in assessing if an abnormality in a mammogram is malignant. Typical characterization features of lesions that are often evaluated to determine malignancy include spiculations, micro-calcifications, mass density and/or mass borders. These characterization features are exemplary only and are not to be considered limiting.

Parameters—algorithmically defined properties related to characterization features. These properties, when quantified, are used to determine if a characterized feature of a lesion is likely to indicate that the lesion is malignant or benign. Typical parameters, which can be used to evaluate characterization features of a lesion, are:

for spiculations—degree of spiculation, symmetry of spiculation and directionality of spiculation.

for a micro-calcification cluster—average shape, variability of brightness, variability of area, variability of length, average proximity, number of neighbors and cluster density.

These parameters are exemplary only and are not to be considered limiting. Parameter definition and calculation are algorithm dependent.

Classifier data—quantified parameters as defined above and/or an overall evaluation of malignancy based on a quantified, weighted and summed set of parameters. The classifier data provides an indication of the likelihood of malignancy of a suspected lesion. The overall bar charts described herein below (see inter alia FIG. 3A below) is a typical, but non-limiting, method of presenting an overall evaluation of malignancy.

Overall evaluation of malignancy—a weighted sum of parameters indicating the likelihood of malignancy. Used interchangeably with terms such as "overall evaluation of the likelihood of malignancy", "overall determination of malignancy", "overall evaluation of the likelihood of disease", "overall evaluation of disease" and the like without any attempt at distinguishing between them. These terms imply an assessment of a possibly pathological condition in a lesion. The overall evaluation or overall determination is correlated with a clinical recommendation.

Clinical recommendation—at least one procedure for further assessment of a lesion noted in a digitized image. The recommendation will be based on the overall likelihood of disease as computed by the system described herein. In the case of lesions denoted in digitized mammograms, these include but are not limited to the following: biopsy, more frequent screening, and screening using other modalities.

SUMMARY OF THE PRESENT INVENTION

It is an object of the present invention to provide a system and method for displaying data which assist a radiologist in diagnosing suspected lesions in mammograms, particularly hard to see or difficult to evaluate lesions.

It is a further object of the present invention to provide a method and a system in which classifier data presented with a mammogram assists in reducing the rate of false negative and false positive diagnoses.

An additional object of the present invention is to provide a nuanced evaluation of malignancy for use by a radiologist in diagnosis. The evaluation of malignancy is effected using a plurality of parameters rather than a single value indicating a binary yes-no evaluation.

Another object of the present invention is to present classifier data relating to a mammogram abnormality that permits easy evaluation of changes in the abnormality over a period of time.

It is a further object of the present invention to provide methods and systems for assisting a radiologist in determining a proper clinical recommendation. The recommendation allows the radiologist to further assess a possible pathological condition in a lesion first noted in an image of living tissue. The tissue involved may be any of many different tissue types and imaging may be effected using any of many different modalities.

Another object of the present invention is to provide methods and systems with which to provide a clinical recommendation to a radiologist by using CAD generated data in combination with conventional analysis of a lesion in imaged living tissue. The clinical recommendation assists the radiologist in further assessing a lesion found in the imaged living tissue.

It is yet another object of the present invention to provide methods and systems with which to provide a clinical recommendation to a radiologist by using CAD generated data in combination with conventional analysis of film mammograms. The clinical recommendation assists the radiologist in further assessing a lesion found in the mammogram.

There is thus provided in accordance with the present invention a method for displaying a computer-generated determination of the likelihood of malignancy of a lesion observed in a mammogram. The method includes the steps of providing a digitized image of the mammogram and displaying the digitized image. It also requires employing an input device to select a region of interest directly on the displayed digitized image. The location of the selected region of interest is communicated to a computer processor. The digitized image is processed using the computer processor so that classifier data of a characterization feature of the lesion in the user-selected region of interest are quantified. The classifier data is comprised of a plurality of parameters and/or a weighted sum of these parameters, the latter representing a computer-generated overall evaluation of the likelihood of malignancy. Finally, the method requires displaying the quantified classifier data relating to the characterization feature in the selected region of interest. The displayed classifier data generally includes a computer-generated overall evaluation of the likelihood of malignancy of the lesion.

Additionally, in accordance with a preferred embodiment of the present invention, the characterization feature is a user-selected characterization feature. Typically, the classifier data are displayed on a part of the display separate from the digitized image. The displayed classifier data can be displayed in one of the following formats: as a sum of weighted parameters, the sum indicating an overall evaluation of malignancy and typically displayed in a multicolor chart format; as a plurality of parameters, either as numerical values or in a multicolor chart format or as both; and both as a sum of weighted parameters, the sum indicating an overall evaluation of malignancy and typically displayed in a multicolor chart format, and as a plurality of parameters. The multicolor charts generally have a non-linear relationship with the quantities they represent.

In an embodiment of the invention, one or more parameters in the classifier data are displayed in the displaying step as a numerical value. The numerical value of the one or more parameters is tracked over time, that is over a series of mammograms taken, for example, over a period of months. The one or more parameters are displayed according to the above described method in each mammogram, and the time series of numerical values assists in determining a malignant abnormality.

In yet another embodiment of the present invention, there is provided a method that requires providing a digitized image of the mammogram and displaying the digitized image. It also requires processing the digitized image using a computer processor so that all classifier data of all characterization features in the digitized image are quantified and stored for later retrieval. The classifier data of each of the features is comprised of a plurality of parameters. An input device is employed to select a region of interest directly on the displayed digitized image. The location of the selected region of interest is communicated to the computer processor. The quantified classifier data related to a characterization feature in the selected region of interest is retrieved from storage. Finally, the quantified classifier data of the characterization featured in the selected region of interest is displayed. The displayed classifier data generally includes a computer-generated overall evaluation of the likelihood of malignancy that assists a user in determining the likelihood of malignancy of a lesion on the mammogram.

There is provided in accordance with another aspect of the present invention a system for displaying a computer-generated determination of the likelihood of malignancy of a lesion in a mammogram. The system includes a mammogram provider for providing a mammogram, an optional digitizer for digitally representing the provided mammogram if the original mammogram is in an analogue format, and a display for displaying the digitized mammogram. It further includes an input device in communication with the display for selectably indicating a region of interest on the displayed digitized mammogram. Additionally, it includes a processor in communication with the display. The processor processes, that is computes and classifies, classifier data related to a characterization feature of a lesion in the digitized mammogram. The digitized mammogram and the selected region of interest are displayed on the display. The display also presents the quantified classifier data related to the characterization feature located in the user-selected region of interest. The displayed classifier data typically includes a computer-generated overall determination of the likelihood of malignancy of the lesion.

In another embodiment of the system, a storage unit is included. The storage unit is in communication with the display and the processor. The classifier data of all characterization features on the mammogram is first processed, that is computed and classified, by a processor and then stored in the storage unit. The classifier data relating to the characterization feature in the selected region of interest is later retrieved from the storage unit and transferred to the display for displaying. It is readily understood that the storage unit could be a part of the processor itself.

In one aspect of the present invention, there is presented a method for providing to a user a clinical recommendation for assessing the pathology of a lesion in living tissue. The method includes the steps of: providing a digitized image of the living tissue; processing the digitized image and computing an overall evaluation of the likelihood of disease; based on the overall evaluation of the likelihood of disease and correlated with it, evaluating a clinical recommendation for further assessing the lesion; and presenting to the user the clinical recommendation.

In an embodiment of this method, the step of processing includes processing the digitized image so that classifier data of a characterization feature of the lesion in the imaged tissue are quantified, and an overall evaluation of the likelihood of disease is computed from the quantified data. This embodiment may also include the step of selecting a characterization feature for which to compute classifier data.

In another embodiment of the method of the present invention, the method further includes the step of selecting a region of interest directly on a displayed digitized image which contains a suspected lesion, and the step of processing includes quantifying classifier data for the suspected lesion. In some instances of this embodiment, the lesion in the user-selected region of interest is displayed in the same color as the overall evaluation of the likelihood of disease when the overall evaluation is displayed in a color chosen from colors in a predetermined multicolor format. In other instances of this embodiment, the step of processing includes processing the digitized image using a computer processor so that all classifier data of all characterization features in the digitized image are quantified and stored for later retrieval. This instance of the embodiment also includes the step of retrieving from storage the quantified classifier data related to a characterization feature in the selected region of interest. In some instances of this embodiment, the step of retrieving includes retrieving the stored classifier data from storage and returning it to the processor before the classifier data is transferred from the processor to a display.

In one embodiment, the clinical recommendation is presented as a verbal message in the form of printed output. In another embodiment, the client recommendation is presented as a numerical score. In still another embodiment of the method of the present invention, the clinical recommendation is presented as an audible signal.

In yet another embodiment of the method of the present invention, the step of presenting includes the step of displaying the clinical recommendation on a display. In instances of this embodiment, the clinical recommendation is displayed as a verbal message.

In a further embodiment, the clinical recommendation is displayed on a part of a display separate from a displayed digitized image. In some instances of this embodiment, the clinical recommendation is displayed in a graphical format. When a graphical format is used, the displayed clinical recommendation may be displayed as a color chosen from a set of colors, each of the colors in the set representing a different clinical recommendation from the other colors in the set.

In yet another embodiment of the method, the displayed clinical recommendation is displayed on a display of the digitized image. In some instances, the displayed clinical recommendation is displayed directly on the displayed digitized image as one element of a predefined set of indicators. The indicators may be chosen from a group consisting of a set of different colors, a set of different sizes, and a set of different shapes, each element of a set representing a different clinical recommendation from the other elements in that set.

In yet another embodiment of the method, the step of presenting includes the step of providing the clinical recommendation over a communications network to at least one distant user.

In a further embodiment of the method of the present invention, the tissue being evaluated is breast tissue. In some instances of this embodiment, the step of providing includes the step of directly providing a digitized image of the breast. In some embodiments of the method relating to breast tissue, the method further includes the step of scoring the lesion found in the digitized image, the scoring effected according to a predefined scoring system intended to indicate the overall likelihood of disease of a lesion found in the digitized image.

In another embodiment relating to breast tissue, the step of providing includes the step of scanning an analogue film mammogram so as to produce a digitized image. This embodiment further includes the step of reading the film mammogram on a light box. In some instances of this embodiment, the method further includes the step of scoring the lesion found in the film mammogram. The scoring is effected according to a predefined scoring system intended to indicate the overall likelihood of disease of a lesion found in the mammogram.

In yet another aspect of the present invention there is presented a system for providing to a user a clinical recommendation for assessing a lesion in imaged living tissue. The system includes an image provider for providing a digital image of the living tissue and a processor operative to receive the digital image from the image provider. The processor computes an overall evaluation of the likelihood of disease in the lesion in the digitized image. It also derives a clinical recommendation correlated with the computed overall evaluation. The system also includes a providing means arranged in data communication with the processor for receiving the clinical recommendation from the processor and for presenting the recommendation to the user.

In some embodiments of the system, the image provider is a digitizer for scanning and digitally representing an image originally in analogue format.

In yet another embodiment of the system, the providing means is a printer and the clinical recommendation is presented as a message on printed output.

In still another embodiment of the system, the providing means for presenting the clinical recommendation is an audible device.

In a further embodiment of the system, the providing means for presenting the clinical recommendation is a set of lights, each light representing a different clinical recommendation.

In another embodiment the providing means is a means for presenting a numerical score.

Another embodiment of the system of the present invention includes a providing means for presenting the clinical recommendation which is a display, the display also displaying the digitized image.

In another embodiment, the system further includes an input device. The device is in communication with the processor and the display. The device can selectably indicate a region of interest on the displayed digitized image, and a clinical recommendation is computed for a lesion in the selected region of interest. In some instances of this embodiment where the providing means is a display, the clinical recommendation is presented as a verbal message on the display. In other instances of this embodiment, the clinical recommendation can be presented as a numerical score on the display. In yet other instances of this embodiment, the clinical recommendation is displayed directly on the digitized image as one element of a pre-selected set of indicators. In cases where indicators are used, the indicators may be chosen from a group consisting of a set of different colors, a set of different sizes, and a set of different shapes. Each element in a set represents a different clinical recommendation from the other elements in that set.

In yet another embodiment of the system of the present invention where the providing means is a display, the displayed clinical recommendation is displayed on a part of the display separate from the digitized image. In some instances of this embodiment, the displayed clinical recommendation is presented as a verbal message on the display. In other instances, the clinical recommendation is presented as a numerical score on the display.

In yet another embodiment of the system of the present invention, the system is in communication with a communications network which provides the clinical recommendation to at least one distant user.

In another embodiment of the system of the present invention, the system further includes a means for entering a score determined by the user, the score indicating the user's evaluation of the expected abnormality of the lesion according to a predetermined scoring system, the score being correlated with a specific clinical recommendation. The user-determined clinical recommendation is then modified by the overall evaluation of the likelihood of disease generated by the system, the modified recommendation provided to the user by the providing means.

In another aspect of the present invention, there is provided a second method. The second method can be used to determine a clinical recommendation for assessing the pathology of a lesion in imaged living tissue. This second method includes the steps of: having the user generate a score for the lesion according to a predefined scoring system, the score indicating the expected abnormality of the lesion and suggesting a clinical recommendation for further assessing the pathology of the lesion; providing a digitized image of the imaged living tissue to a processor; processing the digitized image in a processor so that an overall evaluation of the likelihood of disease is computed for the lesion, a clinical recommendation for further assessing the pathology of the lesion being derived from the overall evaluation and correlated with it; conveying to the user the overall evaluation; and comparing the user-determined score indicating expected abnormality with the processor-computed overall evaluation of the likelihood of disease and using the overall evaluation to modify, according to predetermined criteria, the clinical recommendation suggested by the user-determined score.

In an embodiment of the second method of the present invention, the step of processing includes processing the digitized image so that classifier data of a characterization feature of the lesion in the imaged tissue are quantified, and an overall evaluation of the likelihood of disease is computed from the quantified data. In some instances of this embodiment, the method further includes the step of selecting a characterization feature for which to compute classifier data.

In another embodiment of the second method of the present invention, the step of conveying includes the step of displaying the overall evaluation on a display, the display also displaying the digitized image. In some instances, the overall evaluation is displayed on a part of a display separate from a displayed digitized image. In some of these cases, the overall evaluation is displayed as part of a graphical display. The displayed overall evaluation may be displayed as a color chosen from a set of colors, each of the colors in the set representing a different overall evaluation of disease.

In some instances of this embodiment, the displayed overall evaluation is displayed on the display of the digitized image. In some of these instances, the displayed overall evaluation is displayed directly on the displayed digitized image as an element from a pre-selected set of indicators. The indicators may be chosen from a group consisting of sets of different colors, sets of different sizes, and sets of different shapes, each element of a set representing a clinical recommendation different from the other elements in that set.

In yet another embodiment of the second method of the present invention, the overall evaluation is conveyed as a numeric score in the step of conveying.

In still another embodiment of the second method of the present invention, the method further includes the step of displaying a digitized image and the step of selecting a region of interest directly on the displayed digitized image. There is a suspected lesion in the user-selected region of interest, and quantified classifier data are computed for the lesion. In some instances of this embodiment, the lesion in the user-selected region of interest is displayed in the same color as the overall evaluation of the likelihood of disease when the overall evaluation is displayed in a color chosen from colors in a predetermined multicolor format.

In a further embodiment of the second method of the present invention, the step of processing includes processing the digitized image using a computer processor so that all classifier data of all characterization features in the digitized image are quantified and stored for later retrieval. The embodiment further includes the step of retrieving from storage the quantified classifier data related to a characterization feature in the selected region of interest. In some instances of this embodiment, the step of retrieving includes retrieving the stored classifier data from storage and returning it to the processor before the classifier data is transferred from the processor to a display.

In yet another embodiment of the second method of the present invention, the step of conveying includes the step of providing the clinical recommendation to over a communications network at least one distant user.

In another embodiment of the second method of the present invention, the tissue being evaluated is breast tissue and the digitized image is a mammogram. In some instances of this embodiment, the step of providing includes the step of directly providing a digitized image of the breast. In other instances of this embodiment, the step of providing includes the step of scanning an analogue film mammogram so as to produce a digitized image and further includes the step of reading the film mammogram on a light box prior to generating a score based on the step of reading.

BRIEF DESCRIPTION OF THE DRAWINGS

The present invention will be understood and appreciated more fully from the following detailed description taken in conjunction with the drawings in which:

FIGS. 2A-2F are schematic illustrations of digitized images and classification data relating to the digitized images displayed in accordance with an embodiment of the present invention;

Similar elements in the Figures are numbered with similar reference numerals.

DETAILED DESCRIPTION OF PREFERRED EMBODIMENTS

Figure 1A:
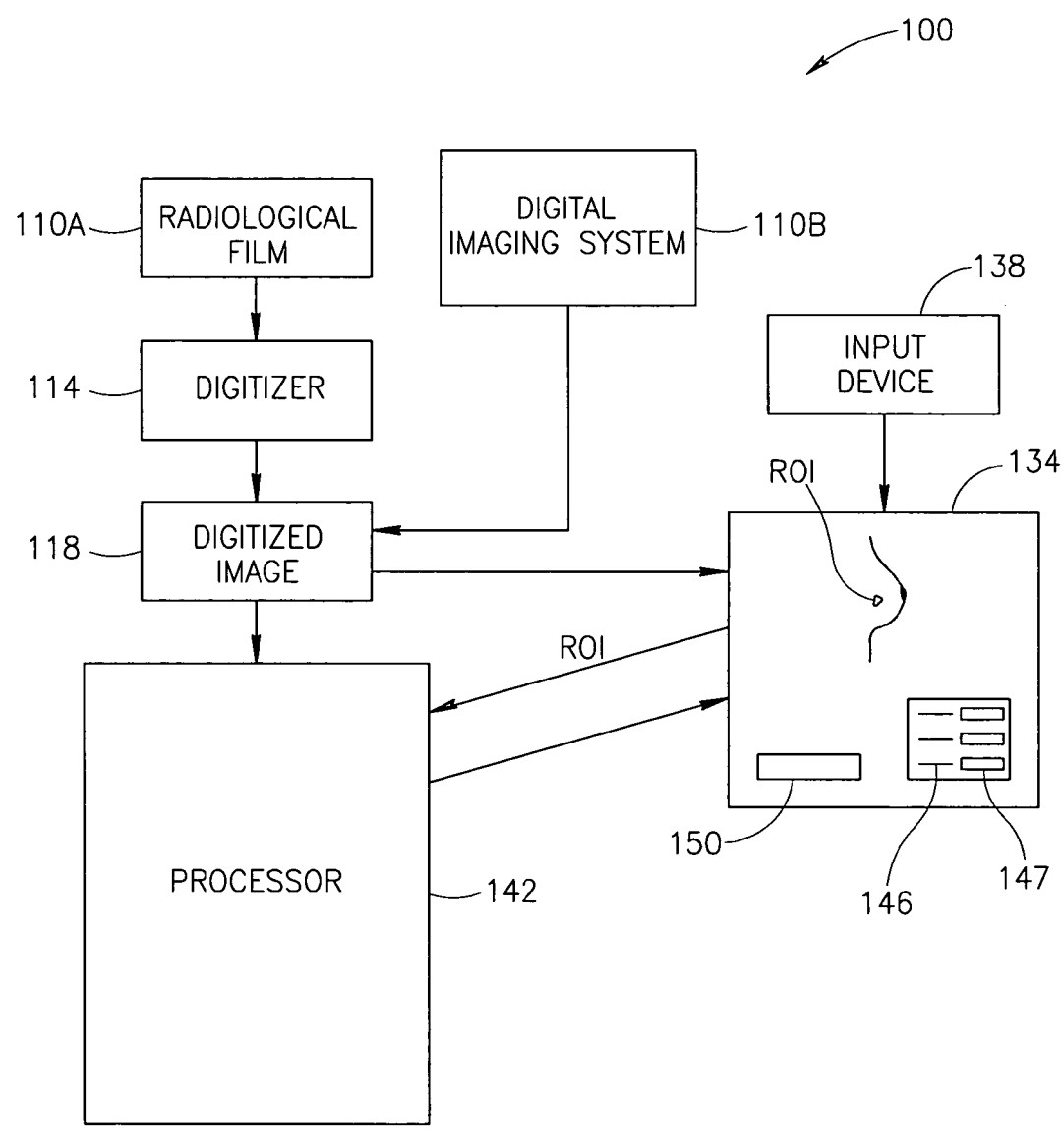
FIGS. 1A and 1B are block diagrams of two embodiments of systems constructed in accordance with the present invention.

The present invention relates to a method and system for displaying digitized mammogram images and diagnosis-assisting information that aids in interpreting the images. More specifically, the invention relates to a computer-aided diagnosis (herein after sometimes denoted as "CAD") method and system for classifying and displaying malignancy evaluation/classification data for anatomical abnormalities in digitized mammogram images. Characterization features of suspected abnormalities in user-selected regions of interest (ROI) are viewed on a display in conjunction with an overall evaluation of malignancy and usually also with a plurality of quantified parameters related to the characterization features. The overall evaluation of malignancy and/or the plurality of quantified parameters are herein also called classifier data. The characterization features viewed and evaluated/classified are also user-selected.

The overall evaluation of a suspected lesion in the radiological images is presented typically, but not necessarily, as a bar chart. The bar chart represents the sum of weighted values of a plurality of predetermined parameters relating to a characterization feature of a suspected lesion located within the user-selected ROI.

The present invention is not intended to detect mammographic abnormalities. The invention is intended to: A. statistically evaluate and classify the malignant or benign character of lesions found within a user-selected ROI, and B. display the quantitative results of that evaluation. In particular, the display of classifier data is intended to assist the radiologist in diagnosing lesions which are hard to see and/or difficult to evaluate visually.

The invention is also intended to provide, directly to a user, a clinical recommendation which is derived from the overall evaluation of malignancy. Additionally, the invention is intended to assist a radiologist in determining a proper clinical recommendation for further assessing a lesion first noted in an image of living tissue.

The method and system of the present invention has several advantages:

1. Prior art displays generally do not provide sufficient information to adequately assist the radiologist with his diagnosis. In the present invention, because numerical values for a plurality of parameters characterizing a suspected anatomical abnormality is presented as well as bar charts for each parameter, the diagnostician has more complete and nuanced information with which to make an informed diagnosis. It should be noted that some of the calculated numerical values can not be intuitively or otherwise easily estimated by a radiologist without the use of a computerized system.

2. In prior art systems, the radiologist is directed to analyze computer determined marked locations on a mammogram. In the present invention, the radiologist determines ROIs that he believes may contain anatomical abnormalities and for which he wishes computer assistance. The radiologist may therefore choose an ROI and analyze the classifier data related to a suspicious lesion within the ROI that would not necessarily be marked by the computer. As a result, the number of missed cancers would be reduced.

3. Prior art systems generally display an overabundance of marked abnormalities without sufficient information to adequately assist the radiologist with his analysis. Because the present invention provides numerical values for a plurality of parameters characterizing a detected anatomical abnormality as well as bar charts for each parameter, the number of false positives is reduced.

4. By looking at the numerical value of a parameter, for example cluster density when viewing micro-calcifications, and comparing it to the numerical value of that parameter in one or more previous mammograms, a non-visual determination can be made for possible malignant changes in the lesion over time. This provides the radiologist with an additional diagnostic tool.

5. A clinical recommendation is derived from the system's overall evaluation of malignancy. The recommendation assists a radiologist in further assessing an abnormality on a mammogram. The clinical recommendation may be directly presented to the user.

Reference is now made to FIG. 1A, which illustrates a system according to an embodiment of the present invention that displays a characterization feature of a suspected lesion on a digitized mammogram image. The feature's associated classifier data, that is quantified classification/diagnostic parameters and/or a quantified overall evaluation/classification of the likelihood of malignancy of the lesion, are also displayed. The system, generally referenced 100, requires a mammogram provider (110A or 110B) to provide a mammogram. The mammogram provider can be a radiological film system 110A which provides a mammogram in analogue format. A digitizer 114 then converts the mammogram into a digitized mammogram image 118. Alternatively, the mammogram provider can be a digital imaging system 110B, discussed further below, which provides a digitized image 118 directly. No digitization by digitizer 114 is required when a digitized imaging system 110B is used. Typically, but without being limiting, the film digitizer 114 is a high resolution charged coupled device (CCD) or laser film digitizer. Digitized image 118 is transferred to a display 134 and to a processor 142. It should readily be understood by one skilled in the art that digitized image 118 could also be transferred to display 134 from processor 142 after image 118 is first sent to processor 142.

A digital imaging system 110B used as mammogram provider may be based on any one of many technologies currently available. These, for example, include, but are not limited to, systems based on magnetic resonance imaging (MRI), computed tomography (CT), scintillation cameras and flat panel digital radiography. All these systems provide radiological mammogram images directly in digital format. If required, the digital mammogram can be reformatted into a digitized mammographic image compatible with processor 142 prior to its being transferred to processor 142.

Processor 142 can employ any of the many algorithms described in the literature to compute and classify parameters associated with the characterization features of breast lesions. The output of processor 142 is usually a quantified value for each of several predetermined parameters associated with the characterization features of the suspected abnormalities, and an overall evaluation of malignancy for the characterization features based on those values. There typically is an evaluation of malignancy correlation for each of the individual parameters as well. Algorithms for use in computing and classifying a plurality of parameters associated with different characterization features of breast abnormalities have been described in the patent and technological literature, some of which have been cited above. Typical algorithms which can be used to determine spiculations, micro-calcifications and/or mass borders are described in U.S. Pat. Nos. 5,854,851 and 5,970,164, both to Bamberger, et al, herein incorporated by reference in their entirety.

A user operated input device referenced 138, such as a computer mouse or touch screen, is in communication with display 134. The user employing the input device indicates directly on the digitized image appearing on display 134 an area of the breast—a region of interest (ROI)—for which he requests assistance in diagnosis. With the aid of the input device, a suspect area of the breast is typically circumscribed by a closed curve. Without being limiting, the curve can be circular, polygonal or elliptical, typically the latter. Information is transferred from display 134 to processor 142 as to the location of the ROI selected on the digitized image. Processor 142 then processes, that is quantifies and classifies, the predefined parameters related to a characterization feature in the user-selected ROI and determines an overall evaluation of malignancy, for the feature. Processor 142 then transfers the overall evaluation of malignancy for the suspected abnormality and/or the individual quantified parameters related to the suspected abnormality to display 134 where they are displayed and can be viewed by the user.

Only areas believed to contain suspected abnormalities and chosen by the user as an ROI have their overall evaluation 150 and quantified parameter information 146 and 147 displayed. Processor 142 does not choose the suspected region; the user alone determines the ROI. This reduces the number of suspected lesions that need to be reviewed, since the number of computer determined lesions generally tends to be far greater than the number of suspicious lesions determined by a radiologist. A bar chart 150 indicating an overall evaluation of malignancy, and/or ancillary numerical values 146, and/or bar chart data 147 for the individual parameters used to arrive at the overall classification are displayed on display 134. The classifier data displayed relates to the characterization feature in the ROI selected. It is readily understood that as the radiologist selects and moves from one ROI to another, a different set of classifier data is displayed.

Display 134 of FIG. 1A shows a complete breast with a selected ROI thereon. Display 134 could also, and usually does, provide an expanded view of the ROI and the characterization feature located within the ROI which is being analyzed. Such an expanded view is shown in FIGS. 2B and 2E discussed herein below.

Without being limiting, the classification data shown on the display is typically presented as a multi-color bar chart 150 or as a multi-color bar chart 150 plus ancillary parameter information 146 and 147. The bar chart 150 is typically composed of three colored regions, one colored region representing a likely benign lesion, one colored region representing a likely malignant lesion, and a colored region between the malignant and benign regions indicating a lesion of indeterminate nature. The malignant region is generally an expanded non-linear region intended to give the user a better, more complete, more nuanced indication of the likelihood of malignancy. An indicator line is positioned along bar chart 150 at the position determined by the computer.

Bar chart 150 represents the overall evaluation of malignancy of the suspected abnormality. Chart 150 represents the sum of weighted values of a plurality of parameters. These parameters are chosen because they are statistically known to correlate with the malignancy of breast lesions. Each parameter is calibrated using a database of radiologist reviewed mammograms. Each characterization feature of a breast lesion, such as spiculation, micro-calcifications and mass density, is based on a different set of predetermined parameters.

The ancillary information, that is information relating to the plurality of independent parameters that are weighted to generate the overall evaluation of malignancy indicated by multicolor bar chart 150, may itself be presented in numerical value 146 and/or bar chart 147 form. As noted above, the presentation of such additional information provides the radiologist with significantly more information than prior art presentations, thereby allowing him to arrive at a more accurate diagnosis.

While what is described herein is described in terms of bar charts, it should be readily evident to one skilled in the art that other equivalent graphical or visual presentations can be used, such as histograms, pie charts, etc. Similarly it is readily evident that what is described herein is only one of many possible bar chart displays.

It was noted above that the user first selects an ROI using input device 138 and then processor 142 processes and computes the classifier data for that portion of the digitized image within the selected ROI. Processor 142 first processes, computes and classifies the classifier data for the selected ROI, transmitting them to display 134. In an alternative embodiment, shown in FIG. 1B to which reference is now made, a system is shown generally referenced 160, in which the parameters associated with all the characterization features for the entire digitized image are processed, computed and classified. This information may then be stored in a storage unit 130 which is separate from, but in communication with, processor 142. It is readily understood by one skilled in the art that, alternatively, storage unit 130 can be constructed to be an integral part of processor 142. After an ROI is selected, the evaluation/classification and parameter information related to the ROI is retrieved from storage unit 130 and sent for display to display 134.

Figure 1B:
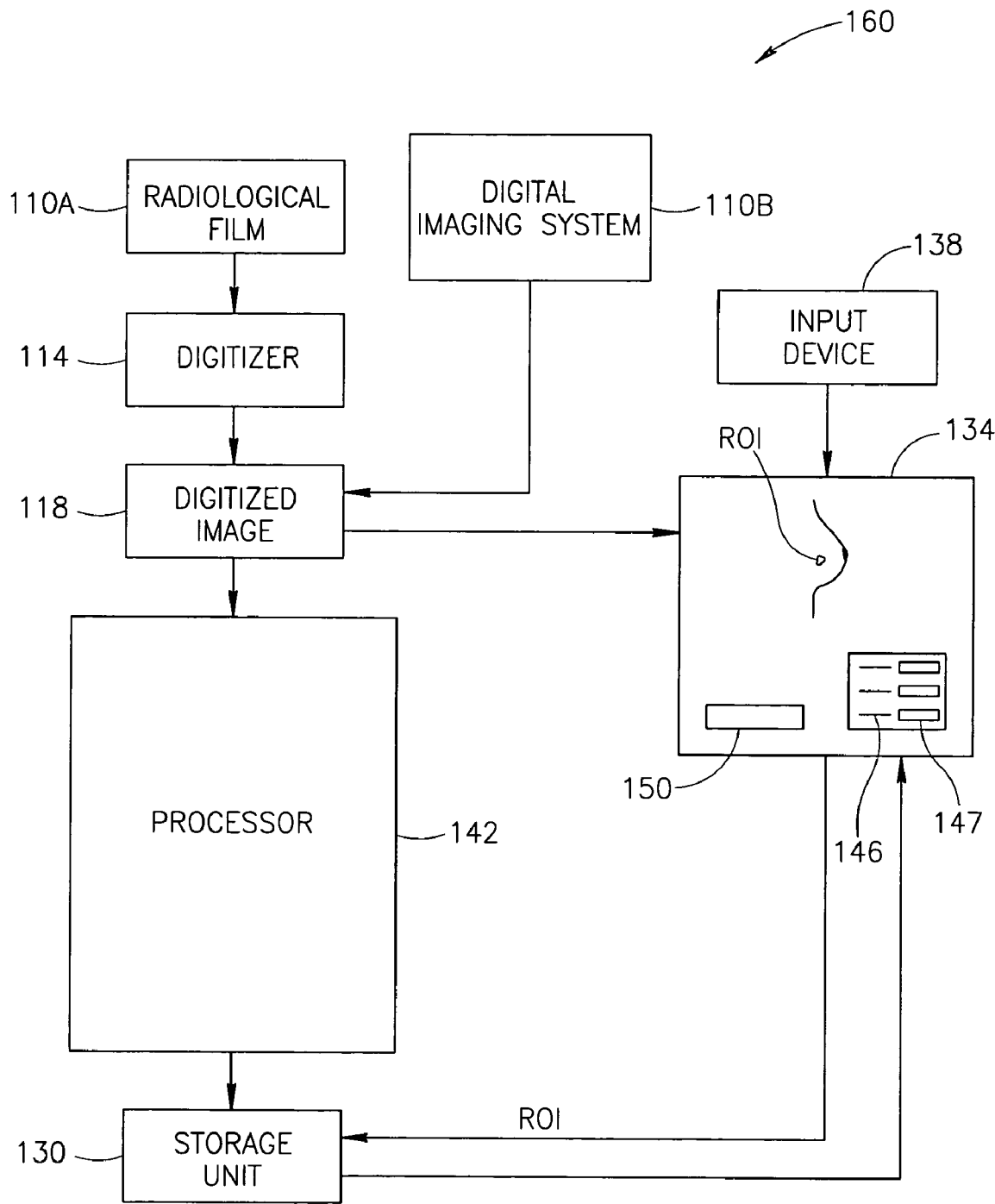

Another embodiment of a system constructed according to the present invention can be considered a hybrid of the embodiments described in conjunction with FIGS. 1A and 1B. Storage unit 130 is in communication with processor 142. When display 134 transfers information about the choice of a user-selected ROI to processor 142, the relevant classifier data is retrieved from storage unit 130 and returned to processor 142 upon a command from the latter. Finally, the retrieved classifier data can be transferred from processor 142 to display 134 for viewing.

Figure 2D:
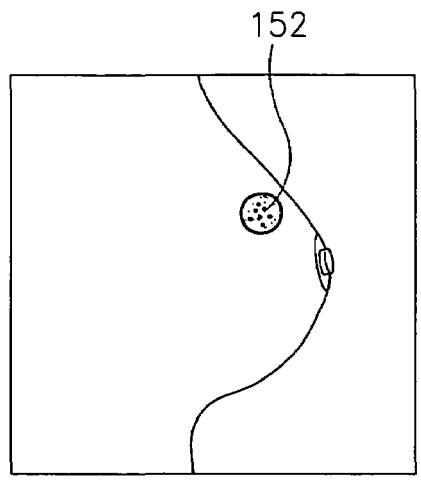
Figure 2E:
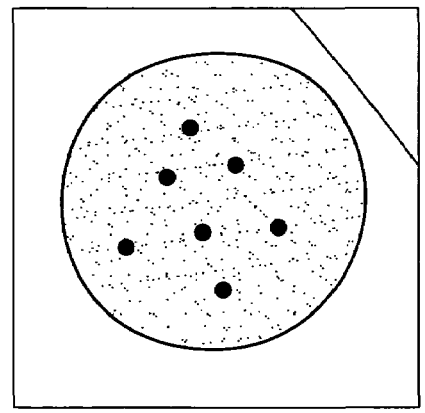

FIGS. 2A-2C and FIGS. 2D-2F, to which reference is now made, illustrate typical displays according to the present invention of two characterization features of breast lesions that may be used to evaluate the malignancy of breast lesions. FIGS. 2A-2C show the display of a digitized mammogram containing spicule lines circumscribed by an ellipse indicating an ROI 154 (FIG. 2A), spicule lines in the selected ROI 154 as displayed by the spiculation visualization tool of the system (FIG. 2B), and a typical display of classifier data relating to the spiculations (FIG. 2C). It should be noted that the spicule visualization tool is not a separate visualization tool but rather a display of the morphological analysis performed for quantification purposes of the image inside ROI 154. The classifier data (FIG. 2C) displayed includes numerical values 146 and bar charts 147 of several different parameters associated with spicule lines, as well as a bar chart 150 indicating the overall evaluation of malignancy of the spiculated lesion. The classifier data is generally displayed below or outside the margins of the displayed spicule lines so as not to interfere with their presentation.

Figure 2F:
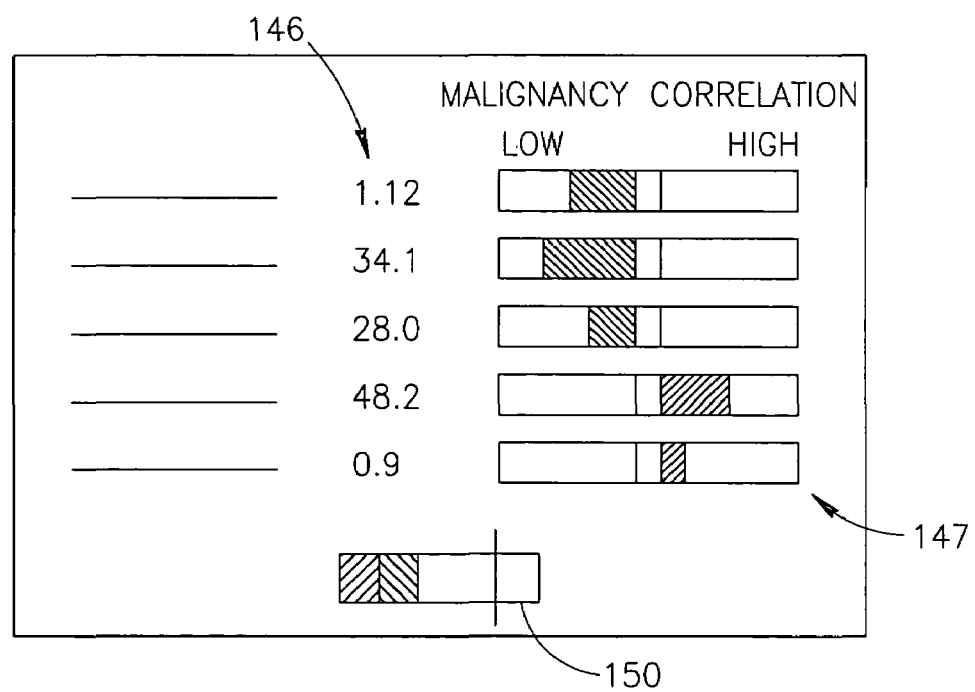

FIGS. 2D-2F illustrate a digitized mammogram (FIG. 2D) containing a cluster of micro-calcifications circumscribed by an ellipse indicating an ROI 152, an enlarged display (FIG. 2E) of ROI 152 containing the cluster, and a display (FIG. 2F) of typical classifier data relating to the displayed micro-calcification cluster. The classifier data of the micro-calcification cluster as displayed in FIG. 2F includes a multi-color bar chart 150 indicating the overall likelihood of malignancy, and numerical values 146 and bar charts 147 for many of the individual parameters used to compute the overall evaluation of the malignancy.

The overall evaluation of malignancy in FIGS. 2C and 2F (shown here as bar charts) is determined by summing the weighted value of a plurality of predetermined parameters, where the parameters are calculated according to the specific algorithm used by processor 142 of FIGS. 1A and 1B. Each parameter has been determined previously to correlate statistically with the malignancy of a lesion. The individual parameters are weighted in the overall score according to their pre-established degree of correlation with malignancy.

In FIGS. 2C and 2F, the individual parameters themselves are shown both as numerical values 146 and as bar charts 147. Each individual bar chart 147 indicates the likelihood of malignancy based on that parameter alone. The extra information provided by this form of display is valuable for the diagnostician in determining the malignancy or non-malignancy of a lesion. An overall evaluation as presented in bar chart 150 supplemented with additional parameter-by-parameter information as provided by numerical values 146 and bar charts 147 allows for more accurate diagnoses than when a single overall value alone is displayed.

As noted above, numerical values also allow for easier tracking of changes in a lesion over time leading to a more accurate diagnosis. Typically, several mammograms would be taken over a time period of several months. The numerical value of a given parameter for a characterization feature of a suspected lesion would be compared for changes over that period when evaluating the malignancy or non-malignancy of the lesion.

Figure 3A:
FIGS. 3A-3E are schematic illustrations of bar charts used to represent the overall evaluation of malignancy of a lesion and the individual parameters used to arrive at the overall evaluation of malignancy in accordance with an embodiment of the present invention.

Reference is now made to FIGS. 3A-3E where the overall evaluation of malignancy bar chart 150 and the individual parameter bar charts 147 discussed above in conjunction with FIGS. 2C and 2F are presented according to an embodiment of the present invention. Bar chart 150 shown in FIG. 3A represents an overall evaluation of malignancy display and is comprised of six colored cells: one green, one yellow, and four red. There is an indicator bar that is positioned along the graph according to the results of the algorithm that indicates the likelihood of malignancy.

As mentioned above, the parameters calculated by the algorithms are weighted and then summed to provide an overall value for the likelihood of malignancy. This weighted sum is reflected in the position of the indicator on bar chart 150. The exact parameters chosen with which to calculate the likelihood of malignancy are a function of the algorithm used while the weighting factors are determined statistically to reflect the likelihood of malignancy. The parameters and weighting factors are different for each characterization feature. The overall evaluation is calculated by using the original values of the chosen parameters and weighting them based on their known statistical correlation with breast malignancies. These weighted scores are then summed.

As a typical non-limiting example, the overall evaluation bar chart 150 shown in FIG. 3A is presented as a bar chart having six colored cells; the leftmost cell being colored green, the second cell from the left being colored yellow and the four rightmost cells being colored red. The overall evaluation/classification relating to the weighted total score is indicated as a black line in one of the cells. The further to the right in the four rightmost cells the greater the likelihood of malignancy. The overall evaluation of malignancy bar chart is non-linear and based on a distribution function of the classifier data for benign and malignant cases. The distribution function is a histogram showing frequency of malignant cases for each value of classifier data. This form of presentation of the overall likelihood of malignancy is more effective than prior art presentations because it provides the radiologist with a more meaningful picture of the malignancy score.

Figure 3B:
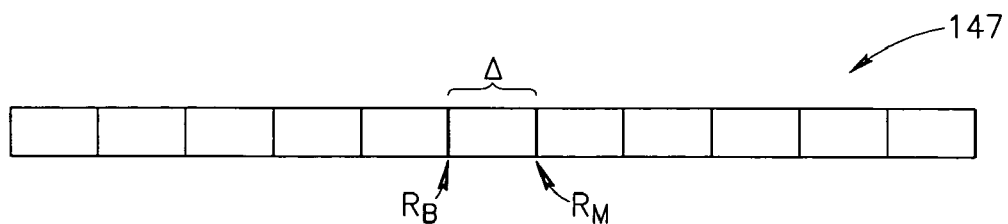

As shown in FIG. 3B, for each parameter, an 11 cell horizontal bar chart 147 is generated on which two reference value lines are displayed, a benign reference value, here designated as Rb, and a malignant reference value, here designated as Rm. The difference between the benign reference value, Rb, and malignant reference value Rm, is designated as delta. The five cells on the left of the benign reference value Rb, refer to benign values while the five cells to the right of the malignant reference value Rm, refer to malignant values. The middle cell represents an indeterminate value. Each cell, except the rightmost and leftmost cells, represents an interval of values equal to delta. The leftmost cell begins at the benign reference value Rb, less 4*delta and extends to infinity. The rightmost cell represents values beginning at the malignant reference value Rm, plus 4*delta and extends to infinity.

Figure 3C:
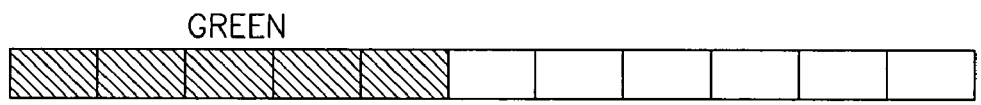
Figure 3D:
Figure 3E:

If the actual value is below the lower reference value, the benign reference value Rb, the cells located between the line representing the benign reference value Rb and the cell corresponding to the actual value are colored green as shown in FIG. 3C. FIG. 3C shows a presentation of results for an "extremely" benign lesion. Similarly, if the actual value is above the upper reference value, the malignant reference value Rm, the cells located between the line representing the malignant reference value Rm, and the cell corresponding to the actual value are colored red as shown in FIG. 3D. FIG. 3D shows a presentation of results for a "moderately" malignant lesion. When the malignancy for a parameter is found to be indeterminate, that is below the malignant reference value and above the benign reference value, the central cell is colored yellow as shown in FIG. 3E.

It is readily understood by one skilled in the art that other methods of graphical presentation can also be used instead of the bar charts in FIGS. 3A and 3B. Similarly, the colors indicated in FIGS. 3A-3E and used in the discussion herein, are exemplary only. The above presentation is a typical, but non-limiting, example. For example, in one variation of the presentation, and for exemplary purposes only, the shade of red can increase in going from a less likely overall evaluation of malignancy to a more likely evaluation of malignancy. Most important is that the presentation indicates small differences in the quantified classifier data, especially the overall evaluation bar chart, and that these differences can be easily noted by the radiologist.

In another embodiment of the present invention, the characterization feature of the lesion being evaluated, for example spicule lines or micro-calcifications, can be presented on the display using a color indicating its malignancy. The characterization feature would have the same color as the color indicated on the overall evaluation of malignancy presentation, typically a bar chart presentation similar to the one discussed in conjunction with FIG. 3A.

Figure 4A:
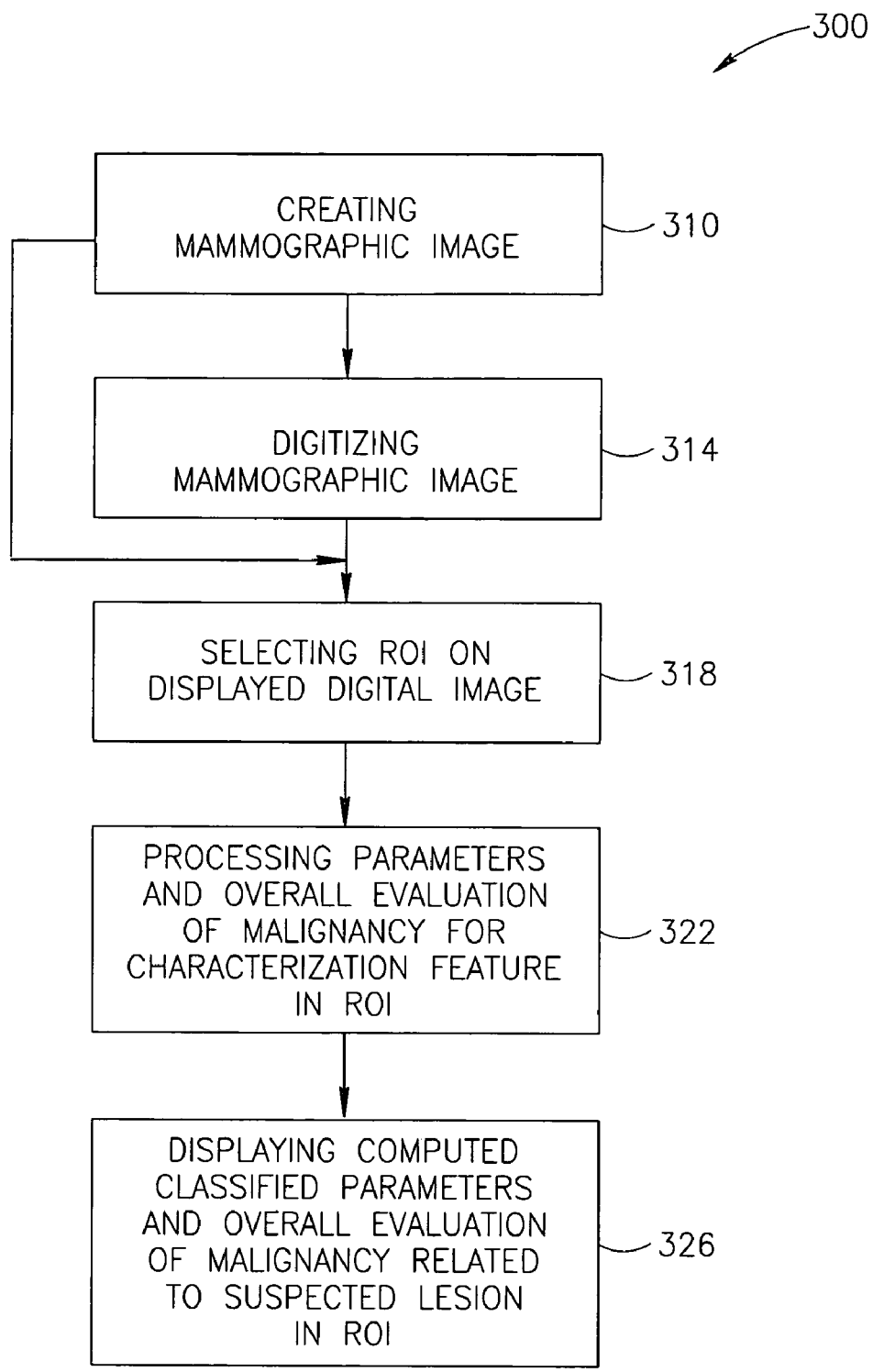
FIGS. 4A and 4B are flow charts of two embodiments of the method of the present invention.
Figure 4B:
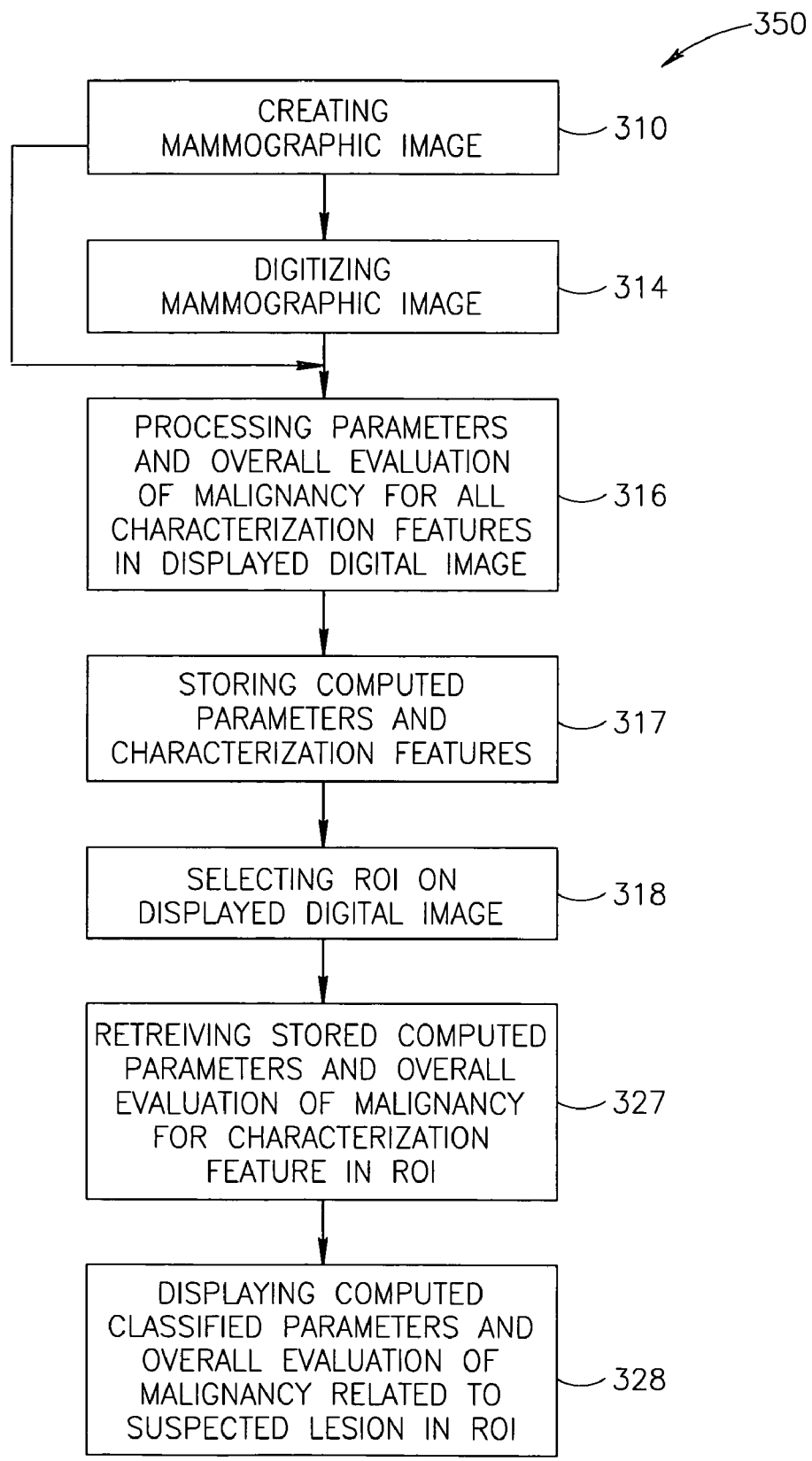

Reference is now made to FIGS. 4A and 4B where two embodiments of the method of the present invention are illustrated. In FIG. 4A, where the method is generally referenced 300, a radiological image is created 310 either by using a digital imaging system or by using a mammogram film system as described above in conjunction with FIG. 1A. The mammographic image is then digitized 314 and displayed. If the mammographic image is already a digitized image, that is if the image has been generated by a digital imaging system as described in conjunction with FIG. 1A above, step 314 does not need to be performed and the image is displayed directly.

The user selects 318 a region of interest (ROI) on the displayed digitized mammographic image for which he requires assistance in diagnosis. Selection is typically, but not necessarily, indicated by circumscribing the ROI on the display with a closed curve. Note that the user diagnostician chooses the ROI and not the CAD system. Accordingly, the number of suspected abnormalities displayed using the CAD is held to a number commensurate with the needs of the user and his ability to comfortably review them.

Processing 322 then ensues. Processing includes identifying the user-selected characterization feature in the user-selected ROI chosen in step 318. It also includes computing all predetermined parameters associated with the characterization feature, classifying the individual parameters as to their likelihood of malignancy, and computing an overall evaluation of malignancy based on the sum of the parameters after weighting them.

For the ROI selected in step 318, an overall evaluation of malignancy is displayed 326 on a display. The overall evaluation of malignancy based on a user-selected characterization feature in the user-selected ROI is displayed, typically but not necessarily, as a bar chart. Other forms of multi-color display are also possible as discussed above. Optionally, but usually, additional data relating to the individual parameters characterizing the characterization feature of the suspected lesion are displayed as numerical data or as multi-color bar charts or as both. Such a display has been discussed above with reference to FIGS. 2C and 2F.

In FIG. 4B, a second embodiment of the method of the present invention is shown, generally referenced 350. It is very similar to the embodiment shown in FIG. 4A. However, in this second embodiment, the processing step 316 is effected prior to the selecting step 318. Processing step 316 includes locating the characterization features, computing their associated parameters, and calculating an overall evaluation of malignancy for each feature based on their associated parameters. This processing is done for the entire digitized image. After processing, the characterization features, their associated parameters and the overall evaluations of malignancy for each characterization feature are stored 317 in a storage unit of the system. As in the embodiment of FIG. 4A, in selection step 318, the user selects an ROI. Then the characterization features and associated parameters for the suspected lesion in the selected ROI are retrieved 327 from storage and displayed 328.

In the system described in conjunction with FIGS. 1A-3F, both bar charts and numerical data are provided which indicate the probability of malignancy of a lesion in a user chosen region of interest. It has been found that numerical data alone does not maximize the benefits of a CAD system. Physicians, even trained physicians, can not readily apply the results of CAD generated numerical data and the probability of malignancy indicated by them. Physicians require additional information to translate "quantitative" data into appropriate clinical recommendations. What has been found is that the overall evaluation of malignancy, typically presented in the present invention as a multi-colored bar chart, can be used to assist the radiologist in determining an appropriate diagnostic course of action.

The following results indicate the advantages of a CAD system that supplies specific clinical recommendations along with "raw" numerical data.

In Tables I and II below, nine radiologists each examined 40 different cases, one set of mammograms for each patient, for which the pathological status of the lesion(s) in the mammograms was independently established by histological examination. The total number of cases evaluated was 360. In half of these cases the lesions were proven to be malignant and in half of the cases the lesions were proven to be benign.

Tables I and II below show the increase in sensitivity and specificity that results when a radiologist uses the clinical recommendations derivable from the overall evaluation of malignancy. The overall evaluation was generated by the CAD system described herein above. Below each table, both sensitivity and specificity results are shown. Sensitivity is the number of actual malignancies the radiologist correctly identified. It represents the complement of the rate of false negatives. Specificity is the number of actual benign cases the radiologist correctly identified and it represents the complement of the rate of false positives.

Table I represents the results when only conventional Breast Imaging Reporting and Data System (BI-RADS®) scoring by the radiologist was used. The conventional scoring procedure was made by the radiologist after viewing analogue film mammograms using a light box.

After reviewing the films, the radiologist assigned a BI-RADS® score as described by the American College of Radiology (ACR) on its Internet site http://www.acr.org. According to the BI-RADS® system, a score of 1 or 2 is assigned if there is no lesion present or if the lesion is definitely benign. A BI-RADS® score of 3 is assigned if the radiologist believes that the lesion is probably benign and the probability of malignancy$\leqq$2%. A BI-RADS® score of 4 is assigned to a suspicious abnormality having a probability of malignancy such that 2%<probability of malignancy<95%. Finally, a score of 5 is assigned to a lesion which is highly suggestive of malignancy (probability of malignancy$\geqq$95%). The BI-RADS® classification advises biopsying all lesions with scores of 4 or greater. There are two additional scores in the BI-RADS® classification but neither requires a biopsy. A score of 6 indicates a verified malignancy after a prior biopsy and a score of 0 indicates a need for additional images or prior mammograms for comparison.

Table I below summarizes the results of conventional light box evaluation with BI-RADS scoring. The false negative rate is about 7% while the false positive rate is about 73%. The latter is typical of the large number of negative results obtained when suspicious lesions seen on mammograms are sent for biopsy. From Table I, we see that the radiologists sent 299 of the 360 cases for histological analysis.

Table II above shows the results and benefits of CAD assisted evaluations. In addition to conventional light box analysis and BI-RADS® scoring, the CAD system described hereinabove was used. In particular, the overall evaluation of malignancy bar chart was used to assist the physician in reassessing his original BI-RADS® score and to modify his clinical recommendation, when necessary.

From Table II, we see that the radiologists sent 274 of the 360 cases for histological analysis. This is a decrease of about 10% from Table I. Table II shows a false negative rate of about 5% and a false positive rate of about 57%. The large decrease in false positives is particularly striking. It is obvious that a reduction in false positives will decrease the amount of unnecessary work in cytology and histology laboratories. More importantly, many women will be spared unnecessary worry about the results of unwarranted biopsies.

TABLE I

Conventional Assessment
Conventional Assessment Using BI-RADS Categories Alone

| Proven Pathological Results | Radiologist Requested Biopsies | Radiologist Forgoes Biopsies | Total |
|---|---|---|---|
| Malignant | 168 | 12 | 180 |
| Benign | 131 | 49 | 180 |
| Total | 299 | 61 | 360 |

Sensitivity = 168/180 = 93.3%
Specificity = 49/180 = 27.2%

TABLE II

CAD Assisted Assessment: Conventional BI-RADS ® Categories are Modified According to the Color Bar of the System of the Present Invention
CAD-Assisted Adjunctive to Conventional BI-RADS ® Categories

| Proven Pathological Results | Radiologist Requested Biopsies | Radiologist Forgoes Biopsies | Total |
|---|---|---|---|
| Malignant | 171 | 9 | 180 |
| Benign | 103 | 77 | 180 |
| Total | 274 | 86 | 360 |

Sensitivity = 171/180 = 95.0%
Specificity = 77/180 = 42.8%

Table II represents the results obtained when the system of the present invention is used as intended. It is envisioned that in an embodiment of the present invention, the CAD system and method of the present invention will be used as an adjunctive technique when suspicious findings are detected using conventional mammographic film and light box examination. Suspicious findings are defined as lesions receiving a BI-RADS® score of 3-5 as described by the American College of Radiology. For cases with such scores, the CAD system and method of the present invention will be applied. Classifier data will be displayed, as will an overall evaluation of the likelihood of malignancy. As discussed above, the overall evaluation of malignancy is a weighted average of a large number of classifier data. A clinical recommendation related to and derived from the displayed overall evaluation of malignancy is abstracted by the physician. The physician then modifies the clinical recommendation suggested by his original BI-RADS® score, as required.

Table III below illustrates the interaction between a pre-CAD assessment BI-RADS® score and a CAD determined overall evaluation of malignancy. This interaction affects the determination of a "final" clinical recommendation. As discussed in conjunction with FIGS. 2A-3F, this overall evaluation, typically but not necessarily, is presented in a tricolor bar chart containing red, yellow and green regions.

TABLE III

Establishing a Clinical Recommendation

| Conventional BI-RADS® Category | Location of Classification Cursor on Bar Chart | Adjunctive BI-RADS® Category | Clinical Recommendation |
|---|---|---|---|
| 3 | Green | 3 | Short-term followup |
| 3 | Yellow | 3 | Short-term followup |
| 3 | Red | 4-5 | Send for biopsy |
| 4 | Green | 3 | Short-term followup |
| 4 | Yellow | 4 | Send for biopsy |
| 4 | Red | 4-5 | Send for biopsy |
| 5 | Green | 3 | Short-term followup |
| 5 | Yellow | 5 | Send for biopsy |
| 5 | Red | 5 | Send for biopsy |

When the overall evaluation is indicated on the bar chart as red, the lesion is deemed to be malignant and a biopsy is recommended. When green is indicated and the lesion has been given a BI-RADS® score of 3 or more, short-term follow-up is recommended. When the bar chart indicates yellow, the system recommends either a biopsy or short-term follow-up depending on the original BI-RADS® score.

Figure 5A:
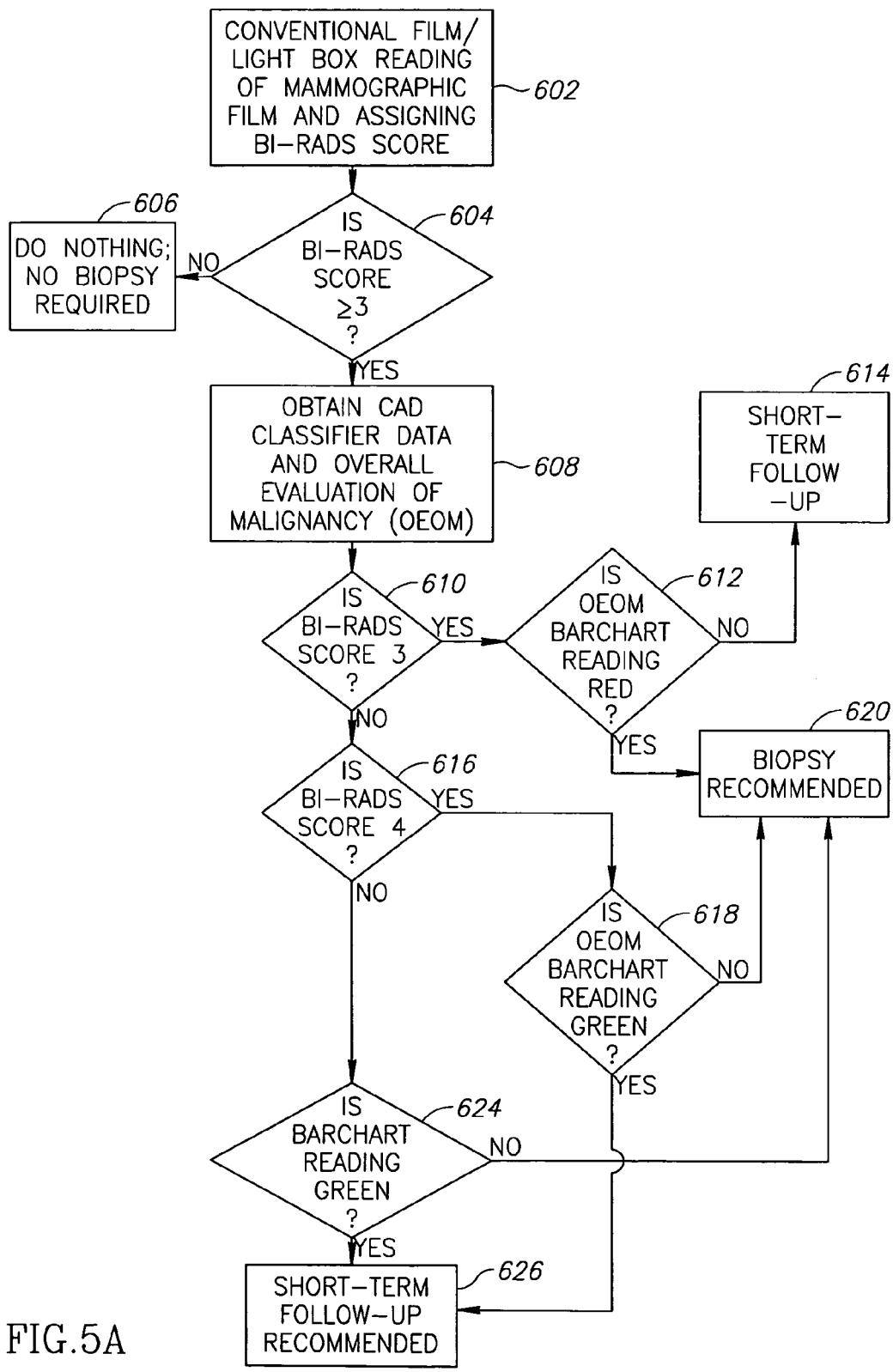
FIG. 5A shows a flowchart of an embodiment of a method of the present invention indicating how the invention may be used to provide a clinical recommendation.

Reference is now made to FIG. 5A in which an embodiment of the method of the present invention is shown. The Figure contains a flowchart that illustrates how to use the CAD display system described hereinabove to determine the proper diagnostic procedure or procedures for further assessing a possibly malignant lesion. The display system provides an implicit clinical recommendation for use as an adjunctive determinant in establishing such a procedure or procedures.

A radiologist examines a patient's film mammograms using a light box and a BI-RADS® score to a lesion found in the films. A determination is made 604 as to whether the score is less than 3. If the score is less than 3, no biopsy is warranted and nothing further is done 606. The radiologist then begins examining 602 a new set of films.

If the score is greater than or equal to 3, the CAD system described above is applied to the films. Classifier data and an overall evaluation of malignancy (OEOM) are computed 608. The OEOM is presented to the user, typically as a bar chart.

A determination is made 610 as to whether the initial BI-RADS® score is 3. If it is 3, a determination is made 612 as to whether the OEOM bar chart indicates red. If it is red, a biopsy is warranted 620. If it is not red, short-term follow-up procedures are suggested 614.

The term "short-term follow-up procedures" as used herein generally means obtaining more frequent mammograms, such as every six months instead of every one to two years. However, it should be understood by one skilled in the art that other, or additional, procedures may be suggested by the radiologist.

If the determination indicates that the BI-RADS® score is not 3, a determination is made 616 as to whether the BI-RADS® score is 4. If the score is 4, a determination is made if the OEOM bar chart indicates 618 a green, benign evaluation. If the bar chart is not green, i.e. it is yellow or red, a biopsy is warranted 620. If it is green, short-term follow-up procedures as discussed above are recommended 626.

If the determination 616 shows that the BI-RADS® score is not 4, i.e. the BI-RADS® score is 5, a determination is made as to whether the bar chart indicates 624 a benign lesion, i.e. the OEOM bar chart reads green. If the bar chart is green, short-term follow-up as discussed above is recommended 626. If the determination does not indicate green, i.e. the bar chart indicates yellow or red, a biopsy is recommended 620.

As can readily be seen in the flowchart of FIG. 5A, there are several instances in which the final course of action is markedly altered by the use of the computer developed recommendation. The flowchart is reflective of the presentation in Table III where the results of the overall evaluation of malignancy as shown on the bar chart modifies the radiologist's initial BI-RADS® score and resulting clinical recommendation.

Figure 5B:
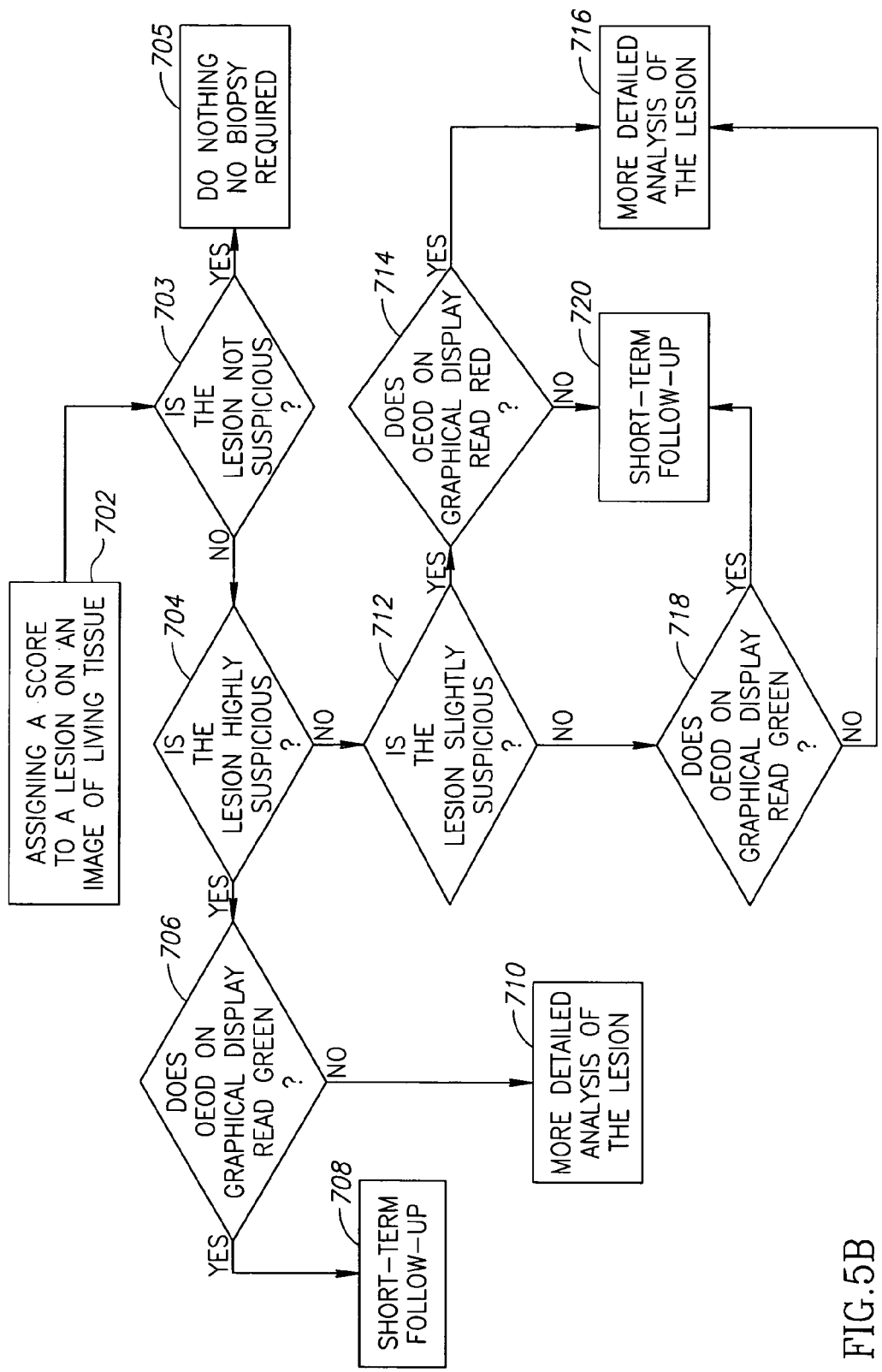
FIG. 5B shows a generic flowchart of an embodiment of a method of the present invention indicating how the invention may be used to provide a clinical recommendation.

FIG. 5B, to which reference is now made, illustrates a more generic representation of the embodiment shown in FIG. 5A. It shows how the present invention may be applied to pathologies in many other tissue types.

The user first assigns 702 a score of a lesion noted on an image of living tissue. The scoring system may be any known system applicable for scoring lesions of the particular nature being evaluated in the specific tissue being examined. The scoring can be done using digitized images or analogue images or digitized images derived from analogue images. Therefore, any modality that produces images used for evaluating lesions in living tissue may be used.

It is next determined 703 whether the lesion is "not suspicious" with respect to a given pathological condition. If the lesion is "not suspicious", nothing is done 705. The definition of the term "not suspicious" will vary from tissue to tissue, lesion to lesion and pathology to pathology. The determination that the lesion is "not suspicious" is made by a physician using conventional analysis of the tissue being evaluated.

If the lesion is suspicious, it is next determined 704 whether the lesion is "highly suspicious" with respect to a pathological condition. The definition of the term "highly suspicious" will vary based on the nature of the lesion examined, the tissue evaluated and the scoring system used. The determination as to "highly suspicious" is made by a physician using conventional analysis of the tissue being evaluated.

When the lesion has been assessed 704 as "highly suspicious" using conventional analysis, a determination is made 706 as to whether the overall evaluation of disease (OEOD) computed by the CAD system is presented as green in the system's graphical display. Green is used here to indicate a low overall evaluation of disease. Similarly, as used herein, red is a high overall evaluation of disease and yellow an intermediate overall evaluation of disease. It is readily understood that other colors and a variety of graphical displays can be used to indicate the overall evaluation of disease.

If the graphical display indicates 708 an OEOD in green, short-term follow-up is suggested. The nature of the short-term follow-up will vary depending on the tissue and pathology being evaluated. If the graphical display does not appear 710 green, more detailed analysis of the lesion, typically cytological or histological analysis, is recommended.

If the lesion is not determined 704 to be "highly suspicious" by the physician, a determination is made 712 as to whether the lesion is only "slightly suspicious" based on the physician's conventional assessment. The definition of the term "slightly suspicious" will vary from tissue to tissue, lesion to lesion and pathology to pathology.

If the physician determines 712 that the lesion is "slightly suspicious", it is then determined 714 if the OEOD is presented in red on the graphical display. If the graphical display is presented in red, a more detailed analysis of the lesion, typically cytological or histological analysis, is recommended 716. If the OEOD is not presented in red, only short-term follow-up is recommended 720. The nature of the short-term follow-up will vary depending on the tissue and pathology being evaluated.

If the physician determines 712 that the lesion is not "slightly suspicious", i.e. it is "moderately suspicious", using conventional assessment, it is then determined if the OEOD graphical display shows 718 a reading of green. If it shows green, only short-term follow-up is recommended 720. If it is determined not to be green, a more detailed analysis of the lesion, typically a cytological or histological analysis, is recommended 716.

It should be understood that in reference to the embodiments of FIGS. 5A and 5B, it is the physician that is integrating his original score for the lesion with the overall evaluation of disease generated by the CAD system. As a result of the latter, the physician modifies the clinical recommendation suggested by his original score as described in Table II. This was the method used in obtaining the "final" clinical recommendation in Table II.

Figure 6A:
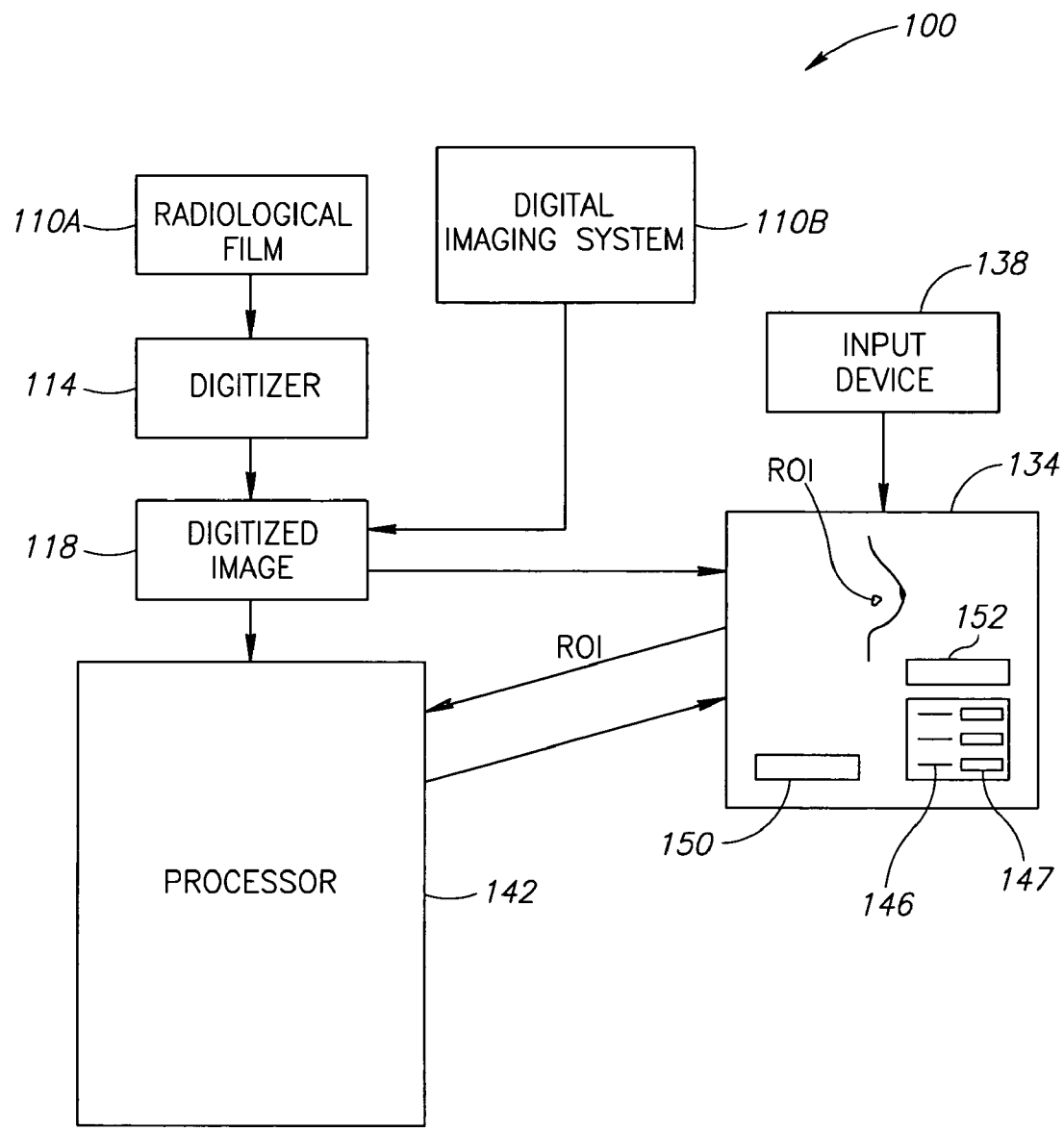
FIGS. 6A and 6B are schematic diagrams of two embodiments of systems constructed in accordance with the present invention used for directly presenting clinical recommendations to a user.
Figure 6B:
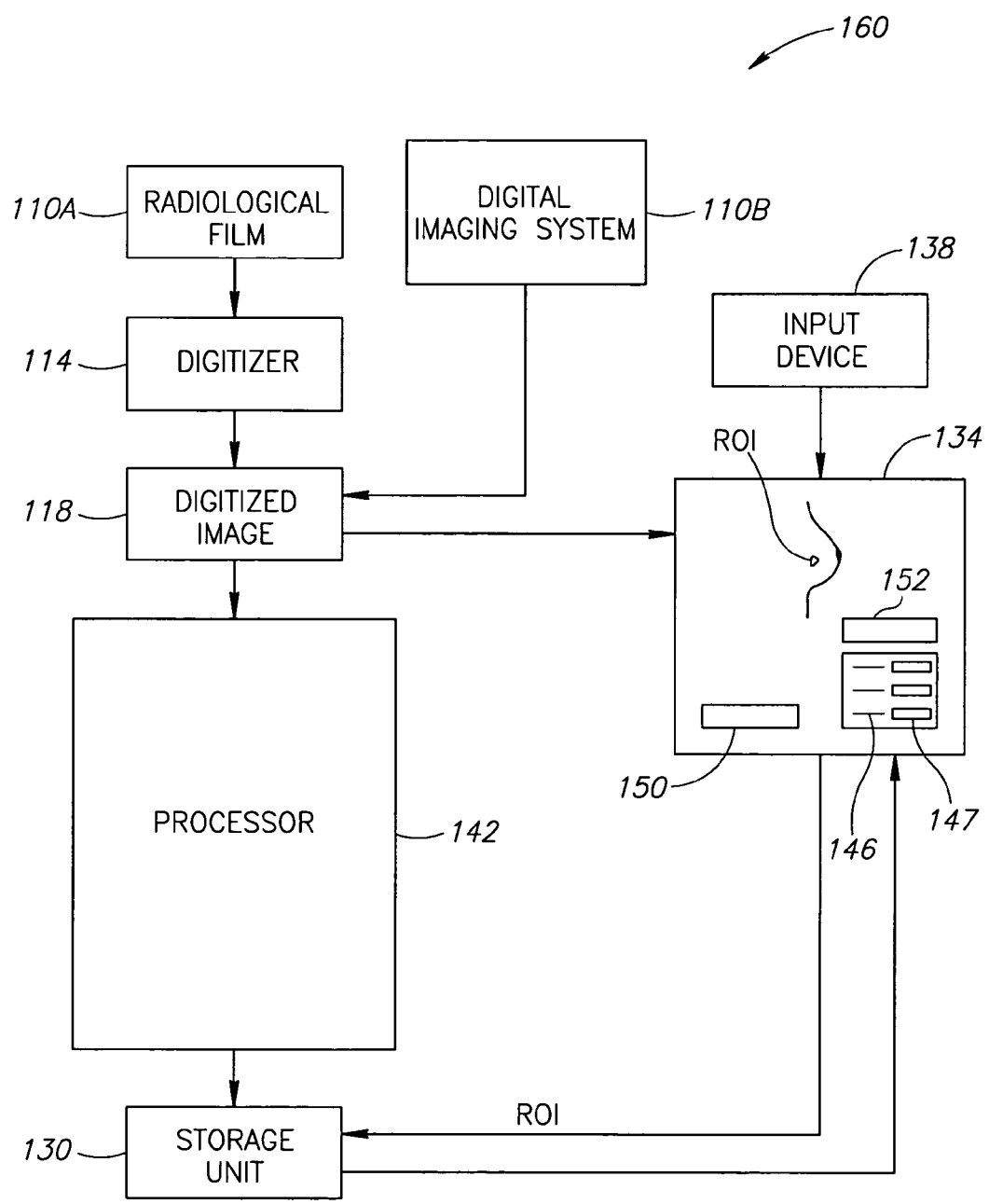

Reference is now made to FIGS. 6A and 6B which illustrate two additional embodiments of the system of the present Invention. They represent systems which can be used to convey directly to the physician the necessary clinical recommendation for a lesion found in a digitized image. They are essentially the systems shown in FIGS. 1A and 1B, respectively. Since these systems have been described above, only the new element 152 in these Figures will be discussed here.

Element 152 can be any of a variety of elements. It may represent a message display configured to provide a verbal message which explicitly reminds the physician that a biopsy is required. It could also provide messages such as "no biopsy recommended", "no recommendation" or "short-term follow-up recommended". A message which indicates one of many options for "short-term follow-up" may also be provided.

It should be remembered that a message display represents only one of many possible means for conveying an appropriate clinical recommendation to a user. In other embodiments, element 152 may represent an audio transmitter that provides an audible signal when a biopsy is required. Alternatively, element 152 can be a series of indicator lights, each of which indicates a different clinical recommendation.

In addition, to providing a clinical recommendation as a verbal message via element 152, in another embodiment the verbal message may be "displayed" by printing it out using an output device. Such an output device is not shown in FIGS. 6A and 6B. Alternatively, the verbal message indicating the clinical recommendation may be directly displayed on display 134. In some embodiments, the recommendation may be displayed directly on a pre-selected region of interest on the digitized image of the breast shown on display 134. In this latter embodiment, the recommendation may be conveyed as different colors, shapes, or sizes for various distinct recommendations.

In other instances, the clinical recommendation may be presented as a computer-generated numerical score, each score related to a specific clinical recommendation. Each score typically is correlated with a probability range for the likelihood of malignancy, each range representing a different recommendation. The numerical score may be presented on a display or other means adapted to provide either a single number or a numerical range representing a specific clinical recommendation.

Other means and elements for directly conveying a clinical recommendation to a physician are also possible and the above list should be considered as exemplary only and non-limiting.

In yet another embodiment, the system can be configured for directly inputting the physician's conventional assessment. The CAD system's processor can then use this assessment in conjunction with its own overall evaluation of disease to provide and directly display a "final" clinical recommendation.

In the case of mammograms, the radiologist's pre-CAD assessment BI-RADS® score could be entered into the system and compared with the system's overall evaluation of malignancy. In what is discussed herein above, the BI-RADS® system has been chosen as the scoring system used in conjunction with the present invention's CAD mammogram assessment. It should be understood that any system or method which is used to generate "not suspicious", "hardly suspicious", "slightly suspicious", "moderately suspicious", "highly suspicious", or other such similar rankings or combinations of rankings, can be used with the CAD assessment described herein. The BI-RADS® scoring system is therefore meant to be illustrative only and not limiting.

In yet another embodiment of the present invention, the system may be in communication with an information network. The message indicating a specific clinical recommendation may be provided by the radiology department via the network directly to the patient's primary care physician.

In the systems of the present invention, such as those shown in FIGS. 6A and 6B, where a direct clinical recommendation is presented to the physician, a correlation is established between the computed overall evaluation of disease and a clinical recommendation. This correlation is established by using a data base of CAD evaluated mammograms, the lesions of which have undergone histological examination in a laboratory. The histological results generally require a definite clinical recommendation. This recommendation is correlated with the observed overall evaluation of disease and stored within the system.

Figure 7A:
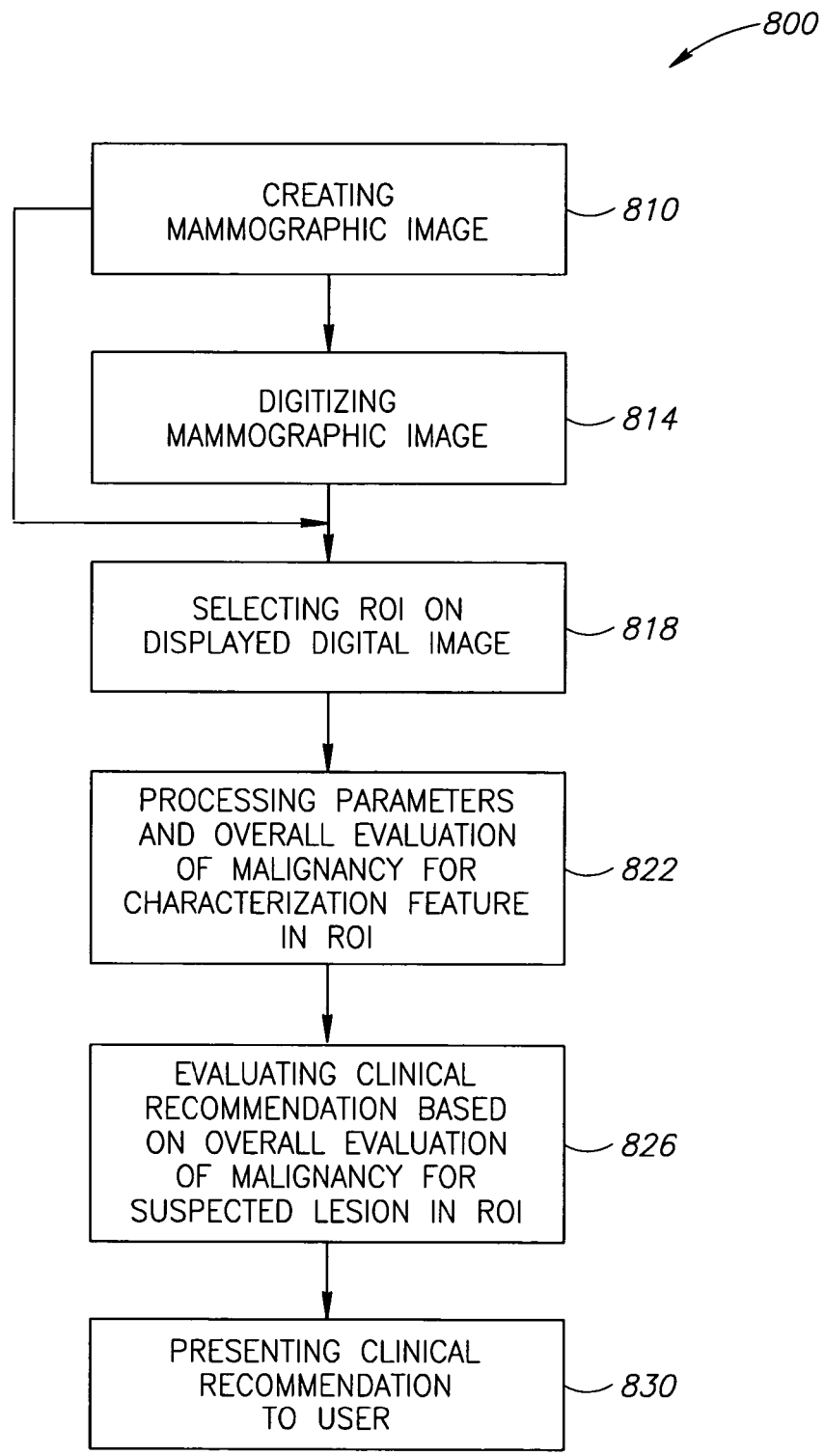
FIGS. 7A and 7B are flow charts of two embodiments of methods of the present invention for directly providing clinical recommendations to a user.
Figure 7B:
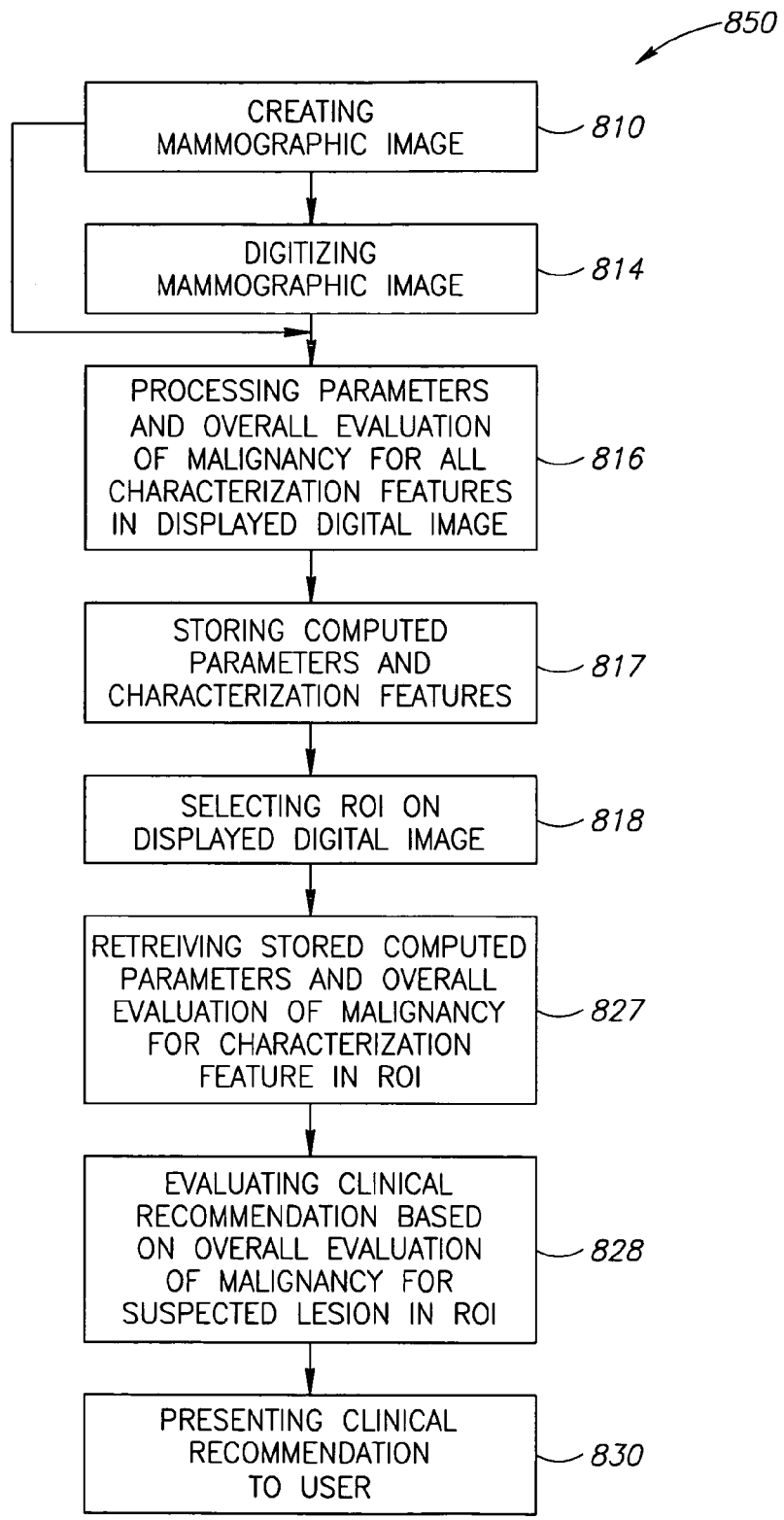

Reference is now made to the flowcharts in FIGS. 7A and 7B which illustrate two additional embodiments of the method of the present invention. In these embodiments, a clinical recommendation is presented directly to the user. As can readily be seen, there are many affinities between the flowcharts in FIGS. 7A and 7B and the flowcharts in FIGS. 4A and 4B, respectively.

In FIG. 7A, where the method is generally referenced 800, a radiological image is created (step 810) either by using a digital imaging system or by using a mammogram film system as described above in conjunction with FIG. 6A. The mammographic image is then digitized (step 814) and displayed. If the mammographic image is already a digitized image, that is if the image has been generated by a digital imaging system as described in conjunction with FIG. 6A above, step 814 does not need to be performed, and the image is displayed directly.

The user selects (step 818) a region of interest (ROI) on the displayed digitized mammographic image for which he requires assistance in diagnosis. Selection is typically, but not necessarily, indicated by circumscribing the ROI on the display with a closed curve.

Processing (step 822) then ensues. Processing includes identifying the user-selected characterization feature in the user-selected ROI chosen in step 818. It also includes computing all predetermined parameters associated with the characterization feature, classifying the individual parameters as to their likelihood of malignancy, and computing an overall evaluation of malignancy based on some mathematical combination of the parameters.

For the ROI selected in step 818, an evaluation of the appropriate clinical recommendation is made in step 826. The evaluation is based on the computed overall evaluation of malignancy. The clinical recommendation is then presented to the user in step 830. The explicit recommendation may include "biopsy", "short-term follow-up", one of the many options for "short-term follow-up", or the like, and conveyed to the user by any of the elements and means described in conjunction with FIGS. 6A and 6B above.

In FIG. 7B, a second embodiment of the method of the present invention, generally referenced 850, is shown. It is very similar to the embodiment that appears in FIG. 7A. However, in the embodiment of FIG. 7B, the step of processing 816 is effected prior to the step of selecting 818. The step of processing 816 includes locating the characterization features, computing their associated parameters, and calculating an overall evaluation of malignancy for each feature based on their associated parameters. This step of processing 816 is done for the entire digitized image. After processing, the characterization features, their associated parameters and the overall evaluations of malignancy for each characterization feature are stored (step 817) in a storage unit of the system. As in the embodiment of FIG. 7A, in selection step 818, the user selects an ROI. Then the characterization features and associated parameters for the suspected lesion in the selected ROI are retrieved (step 827) from storage, a clinical recommendation based on the computed overall evaluation of malignancy of the suspected lesion is evaluated (step 828) and the clinical recommendation is presented (step 830) to the user. Presentation of the clinical recommendation to the user may be affected by any of the elements and means described in conjunction with FIGS. 6A and 6B above.

Generally, the current invention has been discussed above in terms of analogue mammograms which an image digitizer converts to a digital image. Again, it should be remembered that as indicated in FIGS. 1A, 1B, 6A and 6B a direct digital imaging system 110B can be used instead. Digital imaging system 110B will then function as a mammogram provider and may be based on any one of many technologies currently available. These, for example, include, but are not limited to, modalities based on magnetic resonance imaging (MRI), ultrasound (US), computed tomography (CT), scintillation cameras, flat panel digital radiography (DR) and computerized radiography (CR). All these modalities provide breast images directly in digital format. If required, the digital mammogram can be reformatted into a digitized mammographic image compatible with processor 142 (FIGS. 6A and 6B) prior to its being transferred to processor 142. All the methods and systems of display discussed above can be applied to such modalities. Clinical recommendations can be provided as verbal messages, bar charts, numerical scores, audible alerts or in any of the other forms discussed above in conjunction with FIGS. 6A and 6B. Similarly, they can be conveyed by any of the elements and means discussed above.

The above discussion has centered on displays used in systems providing digitized images of the breast. It should be evident to those skilled in the art that such displays, the information they present, and the clinical recommendations they suggest, may be used when imaging other types of tissue. This is true regardless of the method and modalities used. Tissue other than breast tissue that has been, or can be, imaged using various imaging modalities, include inter alia lung, brain, colon and bone tissue. All of the methods and systems discussed herein above may be applied to these other tissue types, with appropriate modification of the various lesion's characterization features, the associated classifier data generated, and the relevant overall evaluation of a pathological condition. The latter can be generated after appropriately calibrating the various systems with images containing lesions of histologically or cytologically proven status.

Table IV below shows other modalities, tissues, and pathologies to which the methods and systems of the present invention may be applied.

TABLE IV

Use of Different Modalities on Different Tissue Systems for Different Pathologies

| Lesion | Modality | Pathology | Characterization Features | Possible Clinical Recommendations |
| --- | --- | --- | --- | --- |
| Lung nodules | CT, Conventional radiography | Malignancy | Presence of calcifications and spiculations, | Biopsy, surgical intervention |
| Lung Tuberculosis | Conventional radiography | Tuberculosis | Size of lesion, extent of disease, number of lesions | Medical treatment |
| Intestinal tumors/ polyps | CT, Virtual colonoscopy | Malignancy | Size, density enhancement due to contrast material, number of lesions | Biopsy, surgical excision, colonoscopy |
| Coronary artery calcified plaque | CT/multislice or electron beam | Infarct | Size and geometry of plaques, number of plaques | Stent, baloon angioplasty, bypass graft |
| Breast tumors | Ultrasound | Malignancy | Shadowing margins of tumors | Biopsy |
| Breast tumors | Magnetic resonance imaging (MRI) | Malignancy | Enhancement due to contrast material, intensity vs. time curve for areas of enhancement | Biopsy |
| Bone tumors | CT, Conventional radiography | Pathological fractures | Volume of tumor, geometry of tumor, thickness of surrounding intact cortex | Radiation therapy, cement injection |

It will be appreciated by persons skilled in the art that the present invention is not limited by what has been particularly shown and described herein above. Rather the scope of the invention is defined by the claims that follow.

What is claimed is:

1. A method for providing to a user a clinical recommendation for assessing the pathological nature of a lesion in living tissue, said method including the steps of:
   providing a digital image of the living tissue for display, the digital image devoid of a computer selected region of interest;
   prior to computer evaluation of the image, user-selecting on the displayed image a region of interest consisting of a portion of the tissue encompassing a single lesion;
   subsequent to said step of selecting, processing the digital image and computing an overall evaluation of the likelihood of disease for the lesion in the user-selected region of interest;
   based on the overall evaluation of the likelihood of disease and correlated therewith, generating a processor-computed explicit clinical recommendation for a further clinical course of action for assessing the lesion, the clinical recommendation usable for patient management; and
   presenting to the user, as separate items of information, both the overall evaluation of likelihood of disease and the explicit clinical recommendation for a further clinical course of action usable for patient management, wherein
   when said tissue is breast tissue said clinical recommendations are chosen from a group of recommendations including biopsy, short term follow-up, specific short term follow-up suggestion, examining the patient using other modalities, and comparing to one or more previous mammograms;
   when said tissue is lung tissue said clinical recommendations are chosen from a group of recommendations including biopsy surgical intervention, medical treatment, short term follow-up, and comparing to one or more previous examinations;
   when said tissue is intestinal tissue said clinical recommendations are chosen from a group of recommendations including biopsy, surgical excision, and colonoscopy;
   when said tissue is coronary artery tissue said clinical recommendations are chosen from a group of recommendations including use of a stent, performing balloon angioplasty, performing a bypass graft, and examining the patient using other modalities; and
   when said tissue is bone tissue said clinical recommendations are chosen from a group of recommendations including surgical intervention, medical treatment, short term follow-up, comparing to one or more previous examinations, radiation therapy and cement injection.

2. A method according to claim 1, wherein the tissue being evaluated is breast tissue.

3. A method according to claim 2 wherein said step of providing includes the step of directly providing a digital image of the breast and wherein said method further includes the following additional steps:
   inputting into a processor a score corresponding to a user evaluated overall likelihood of disease and a user evaluated clinical recommendation relating to the lesion found in the digital image; and
   following the inputting of the score in said step of inputting, modifying the score in accordance with a processor generated clinical recommendation so as to produce a final clinical recommendation,
   and wherein said step of presenting includes displaying the final clinical recommendation to the user.

4. A method according to claim 2, wherein said step of providing includes the step of scanning an analogue film mammogram so as to produce a digital image and wherein said method further includes the step of reading the film mammogram on a light box and wherein said method further includes the following additional steps:
   inputting into a processor a score corresponding to a user evaluated overall likelihood of disease and a user evaluated clinical recommendation relating to the lesion found in the film mammogram; and
   following the inputting of the score in said step of inputting, modifying the score in accordance with a processor generated clinical recommendation so as to produce a final clinical recommendation,
   and wherein said step of presenting includes displaying the final clinical recommendation to the user.

5. A system for providing to a user a clinical recommendation for assessing a lesion in imaged living tissue, said system including:
   an image provider for providing a digital image of the living tissue, the digital image devoid of a computer selected region of interest;
   a display for displaying the digital image of the tissue;
   a user operated input device in communication with said display for selectably indicating on the displayed digital image a user-selected region of interest, the user-selected region of interest being a portion of the breast encompassing a single lesion of interest;
   a processor operative to receive the digital image from said image provider, said processor computing an overall evaluation of the likelihood of disease of the lesion in the user-selected region of interest on the digital image and said processor also deriving an explicit clinical recommendation for a further clinical course of action usable for patient management correlated with the computed overall evaluation for the lesion in the user-selected region of interest; and
   providing means arranged in data communication with said processor for receiving therefrom the overall evaluation of the likelihood of disease of the lesion and the clinical recommendation and for presenting to the user, as two separate pieces of information both the overall evaluation of the likelihood of disease of the lesion and the explicit clinical recommendation suggesting a clinical course of action for assessing the lesion in the user-selected region of interest, the clinical recommendation usable for patient management,
   wherein said processor initiates processing after the region of interest is selected by the user, and
   wherein when said tissue is breast tissue said clinical recommendations are chosen from a group of recommendations including biopsy, short term follow-up, specific short term follow-up suggestion, screening using other modalities, examining the patient using other modalities, and comparing to one or more previous mammograms;
   when said tissue is lung tissue said clinical recommendations are chosen from a group of recommendations including biopsy, surgical intervention, medical treatment, short term follow-up, and comparing to one or more previous examinations;
   when said tissue is intestinal tissue said clinical recommendations are chosen from a group of recommendations including biopsy, surgical excision, and colonoscopy;

when said tissue is coronary artery tissue said clinical recommendations are chosen from a group of recommendations including use of a stent, performing balloon angioplasty, performing a bypass graft and examining the patient using other modalities; and when said tissue is bone tissue said clinical recommendations are chosen from a group of recommendations including surgical intervention, medical treatment, short term follow-up, comparing to one or more previous examinations, radiation therapy, and cement injection.

6. A system according to claim 5, said system further including a means for entering a score determined by the user, the score indicating the user's evaluation of the level of suspicion of the lesion according to a predetermined scoring system, the score correlated with a specific clinical recommendation for a further clinical course of action for assessing the lesion, wherein the user-determined clinical recommendation is modified by the overall evaluation of the likelihood of disease generated by said processor, the modified clinical recommendation being displayed to the user by said providing means.

7. A method for providing to a user a clinical recommendation for assessing the pathological nature of a lesion in living tissue, said method including the steps of:

providing a digital image of the living tissue for display, the digital image devoid of a computer selected region of interest;

prior to computer evaluation of the image, user-selecting on the displayed image a region of interest consisting of a portion of the tissue encompassing a single lesion;

subsequent to said step of selecting, processing the digital image and computing an overall evaluation of the likelihood of disease for the lesion in the user-selected region of interest;

based on the overall evaluation of the likelihood of disease and correlated therewith, generating a processor-computed explicit clinical recommendation for a further clinical course of action for assessing the lesion, the clinical recommendation usable for patient management; and presenting to the user the explicit clinical recommendation for a further clinical course of action usable for patient management, wherein when said tissue is breast tissue said clinical recommendations are chose from a group of recommendations including biopsy, short term follow-up, specific short term follow-up suggestion, examining the patient using other modalities, and comparing to one or more previous mammograms;

when said tissue is lung tissue said clinical recommendations are chosen from a group of recommendations including biopsy, surgical intervention, medical treatment, short term follow-up, and comparing to one or more previous examinations;

when said tissue is intestinal tissue said clinical recommendations are chosen from a group of recommendations including biopsy, surgical excision, and colonoscopy;

when said tissue is coronary artery tissue said clinical recommendations are chosen from a group of recommendations including use of a stent, performing balloon angioplasty, performing a bypass graft, and examining the patient using other modalities; and when said tissue is bone tissue said clinical recommendations are chosen from a group of recommendations including surgical intervention, medical treatment, short term follow-up, comparing to one or more previous examinations, radiation therapy, and cement injection.

8. A system for providing to a user a clinical recommendation for assessing a lesion in imaged living tissue, said system including:

an image provider for providing a digital image of the living tissue, the digital image devoid of a computer selected region of interest;

a display for displaying the digital image of the tissue;

a user operated input device in communication with said display for selectably indicating on the displayed digital image a user-selected region of interest, the user-selected region of interest being a portion of the breast encompassing a single lesion of interest;

a processor operative to receive the digital image from said image provider, said processor computing an overall evaluation of the likelihood of disease of the lesion in the user-selected region of interest on the digital image and said processor also deriving an explicit clinical recommendation for a further clinical course of action usable for patient management correlated with the computed overall evaluation for the lesion in the user-selected region of interest; and providing means arranged in data communication with said processor for receiving therefrom the overall evaluation of the likelihood of disease of the lesion and the clinical recommendation and for presenting to the user the explicit clinical recommendation suggesting a clinical course of action for assessing the lesion in the user-selected region of interest, the clinical recommendation usable for patient management, wherein said processor initiates processing after the region of interest is selected by the user, and wherein when said tissue is breast tissue said clinical recommendations are chosen from a group of recommendations including biopsy, short term follow-up, specific short term follow-up suggestion, screening using other modalities, examining the patient using other modalities, and comparing to one or more previous mammograms;

when said tissue is lung tissue said clinical recommendations are chosen from a group of recommendations including biopsy, surgical intervention, medical treatment, short term follow-up and comparing to one or more previous examinations;

when said tissue is intestinal tissue said clinical recommendations are chosen from a group of recommendations including biopsy, surgical excision, and colonoscopy;

when said tissue is coronary artery tissue said clinical recommendations are chosen from a group of recommendations including use of a stent, performing balloon angioplasty, performing a bypass graft, and examining the patient using other modalities; and when said tissue is bone tissue said clinical recommendations are chosen from a group of recommendations including surgical intervention, medical treatment, short term follow-up, comparing to one or more previous examinations, radiation therapy, and cement injection.

* * * * *